US005840517A

United States Patent [19]

Atkinson et al.

[11] Patent Number: 5,840,517
[45] Date of Patent: *Nov. 24, 1998

[54] PROCESS FOR PREPARING OBESITY PROTEIN ANALOGS

[75] Inventors: Paul Robert Atkinson, Indianapolis; Lisa Kay Foster, Greenwood; Thomas Charles Furman, Indianapolis; Warren Cameron MacKellar, Plainfield, all of Ind.

[73] Assignee: Eli Lilly and Company, Indianapolis, Ind.

[ * ] Notice: The term of this patent shall not extend beyond the expiration date of Pat. No. 5,614,379.

[21] Appl. No.: 823,104

[22] Filed: Mar. 24, 1997

Related U.S. Application Data

[63] Continuation-in-part of Ser. No. 429,362, Apr. 26, 1995, Pat. No. 5,614,379.
[51] Int. Cl.$^6$ ..................................................... C12P 21/02
[52] U.S. Cl. ......................... 435/68.1; 435/176; 435/177; 435/212; 435/223
[58] Field of Search .................................. 435/68.1, 212, 435/223, 176, 177

[56] References Cited

U.S. PATENT DOCUMENTS

| 5,126,249 | 6/1992 | Becker et al. ............................ 435/68.1 |
| 5,614,379 | 3/1997 | MacKellar ............................... 435/68.1 |

FOREIGN PATENT DOCUMENTS

| 0 217 814 | 5/1990 | European Pat. Off. ........ C12P 21/06 |
| 0 397 420 | 5/1990 | European Pat. Off. ........ C12P 21/00 |
| 0 659 886 | 6/1995 | European Pat. Off. . |
| 0 725 078 | 8/1996 | European Pat. Off. ........ C07K 14/47 |
| 0 725 079 | 8/1996 | European Pat. Off. ........ C07K 14/47 |
| WO96/05309 | 2/1996 | WIPO . |

OTHER PUBLICATIONS

Zhang, et al., "Positional cloning of the mouse obese gene and its human homologue", *Nature,* 372:1, 425–432 (Dec. 1, 1994).

Rink, "In search of a satiety factor", *Nature,* 372:1, 406–407 (Dec. 1, 1994).

Flam, "Obesity Gene Discovery May Help Solve Weighty Problem", *Science,* 266, 1477–1478 (Dec. 2, 1994).

Chan, et al., "Dipeptidyl–Aminopeptidases and Aminopeptidases in *Dictyostelium discoideum*", *Biochemical and Biophysical Research Communications,* 127:3, 962–968 (Mar. 29, 1985).

Chan, et al., "Partial Purification and Characterization of Dipeptidyl–aminopeptidase III from *Dictyostelium discoideum*", *Experimental Mycology,* 11, 27–35 (1987).

Hutchinson, et al., "The preparation and properties on immobilised dipeptidyl–aminopeptidase I (cathepsin C)"*Biochimica et Biophysica Acta,* 916, 1–4 (1987).

Erickson, et al., "Interaction of Purified Brush–Border Membrane Aminopeptidase N and Dipeptidyl Peptidase IV with Lectin–Sepharose Derivatives", *Biochimica et Biophysica Acta,* 743, 37–42 (1983).

Huang, et al. "The Purification, Specificity, and Role of Dipeptidyl Peptidase III in *Dictyostelium discoideum*", *Experimental Mycology,* 16, 102–109 (1992).

*Primary Examiner*—Herbert J. Lilling
*Attorney, Agent, or Firm*—James J. Kelley; Steven P. Caltrider; David E. Boone

[57] ABSTRACT

The present invention is directed to an improved process for preparing in high yield an obesity protein analog using a dipeptidylaminopeptidase isolated from the slime mold, *Dictyostelium discoideum.*

15 Claims, No Drawings

PROCESS FOR PREPARING OBESITY PROTEIN ANALOGS

This application is a continuation-in-part of U.S. Ser. No. 08/429,362, filed Apr. 26, 1995 now U.S. Pat No. 5,614,379.

BACKGROUND OF THE INVENTION

1. Field of the Invention.

This invention is in the field of enzyme technology. More specifically, this invention concerns a process for preparing an obesity protein analog using dipeptidylaminopeptidase isolated from the slime mold, Dictyostelium discoideum.

2. Background Information.

Obesity is a common and very serious public health problem in the United States and throughout the world. A naturally-occurring obesity protein, which is encoded by the ob gene, has demonstrated an ability to effectively regulate adiposity in mice [Pelleymounter, et al., *Science* 269:540–543 (1995)]. Analogs of the obesity protein that have improved functionality or stability relative to naturally-occurring obesity proteins are disclosed in Basinski et al., U.S. Ser. No. 08/383,638 and DiMarchi et al., U.S. provisional application numbers 60/000,450 and 60/002,161. Efficient means of producing large quantities of obesity protein analogs are necessary if an obesity protein analog is to become a pharmaceutical product that will impact the large segment of our population that is obese.

The slime mold, *Dictyostelium discoideum*, produces a dipeptidylaminopeptidase, called dDAP, that has been disclosed and claimed in U.S. Pat. Nos. 5,565,330, 5,565,349, and 5,573,923. Processes to produce proteins of SEQ ID NO:1 from proteins of SEQ ID NO:2 using dDAP are disclosed and claimed [U.S. Ser. No. 08/429,362, filed Apr. 26, 1995].

Obesity protein analogs other than those of SEQ ID NO:1 may be produced from obesity protein analog precursors by contacting said obesity protein analog precursors with dDAP. It has further been discovered that when urea is included in the reaction mixture with dDAP and an obesity protein analog precursor, the reaction rate of dipeptidyl cleavage catalyzed by dDAP is greatly enhanced. Finally, the pH optimum of the reaction catalyzed by dDAP is shifted toward a more neutral range in the presence of urea.

SUMMARY OF THE INVENTION

The present invention provides a process for preparing an obesity protein analog, which comprises contacting an obesity protein analog precursor with dDAP.

The present invention further provides a process for preparing an obesity protein analog, which comprises contacting an obesity protein analog precursor with dDAP in the presence of urea.

Finally, the present invention also provides a process for preparing a protein represented by SEQ ID NO:1, which comprises contacting a protein represented by SEQ ID NO:2 with dDAP in the presence of urea.

DETAILED DESCRIPTION OF THE INVENTION

For purposes of the present invention, as disclosed and claimed herein, the following terms and abbreviations are as defined below.

Conversion or conversion reaction—refers specifically to the reaction catalyzed by dDAP whereby dipeptides are removed from the N-terminus of an obesity protein analog precursor to yield an obesity protein analog.

dDap—a dipeptidylaminopeptidase, isolated from *Dictyyostelium discoideum*, which demonstrates a pH optimum of about pH 3.5 with GFpNA as a substrate, in the absence of urea, and has a native molecular weight of about 225,000 daltons, as measured by analytical ultracentrifugation, and a subunit molecular weight of about 66,000 daltons, as measured by SDS polyacrylamide gel electrophoresis.

dDAP bed—any amount of dDAP immobilized to a single or multiple support surface that forms an aggregate volume or unit of immobilized dDAP.

GFpNA—Gly-Phe p-nitroanilide, which serves as a convenient substrate for testing dDAP activity.

Naturally-occurring obesity protein—refers to a protein whose amino acid sequence is identical to the sequence of an obesity protein produced from a mammalian obesity gene following transcription and deletion of introns, translation to a protein, and processing to the mature protein with secretory signal peptide removed, e.g., from the N-terminal valine-proline to the C-terminal cysteine of the mature protein. The sequences of the following naturally-occurring obesity proteins are known: mouse and human [Zhang, et al. *Nature* 372:425–432 (1994)]; rat [Murakami, et al., *Biochem. Biophys. Res. Comm.* 209:944–952 (1995)]; porcine and bovine [EP 0 743 321, published Nov. 20, 1996]; and various primates [U.S. Pat. application Ser. No. 08/710,483 and EP 0764722, published 25 Mar. 1997]. For purposes of this invention, a naturally-occurring obesity protein may be produced in a recombinant organism.

SEQ ID NO:1 refers to proteins of the formula:

| 1 | | | | 5 | | | | | 10 | | | | | 15 | |
|---|---|---|---|---|---|---|---|---|---|---|---|---|---|---|---|
| Val | Pro | Ile | Xaa | Lys | Val | Xaa | Asp | Asp | Thr | Lys | Thr | Leu | Ile | Lys | Thr |

| | | | | 20 | | | | | 25 | | | | | 30 | | |
|---|---|---|---|---|---|---|---|---|---|---|---|---|---|---|---|---|
| Ile | Val | Thr | Arg | Ile | Xaa | Asp | Ile | Ser | His | Xaa | Xaa | Ser | Val | Ser | Ser |

| | | 35 | | | | | 40 | | | | | 45 | | | |
|---|---|---|---|---|---|---|---|---|---|---|---|---|---|---|---|
| Lys | Xaa | Lys | Val | Thr | Gly | Leu | Asp | Phe | Ile | Pro | Gly | Leu | His | Pro | Ile |

| | 50 | | | | | 55 | | | | | 60 | | | | |
|---|---|---|---|---|---|---|---|---|---|---|---|---|---|---|---|
| Leu | Thr | Leu | Ser | Lys | Xaa | Asp | Xaa | Thr | Leu | Ala | Val | Tyr | Xaa | Xaa | Ile |

| 65 | | | | | 70 | | | | | 75 | | | | | 80 |
|---|---|---|---|---|---|---|---|---|---|---|---|---|---|---|---|
| Leu | Thr | Ser | Xaa | Pro | Ser | Arg | Xaa | Val | Ile | Xaa | Ile | Ser | Xaa | Asp | Leu |

| | | | | 85 | | | | | 90 | | | | | 95 | |
|---|---|---|---|---|---|---|---|---|---|---|---|---|---|---|---|
| Glu | Xaa | Leu | Arg | Asp | Leu | Leu | His | Val | Leu | Ala | Phe | Ser | Lys | Ser | Cys |

```
                    100                    105                    110
His  Leu  Pro  Xaa  Ala  Ser  Gly  Leu  Glu  Thr  Leu  Xaa  Ser  Leu  Gly  Gly 115                    120                    125
Val  Leu  Glu  Ala  Ser  Gly  Tyr  Ser  Thr  Glu  Val  Val  Ala  Leu  Ser  Arg 130                    135                    140
Leu  Xaa  Gly  Ser  Leu  Xaa  Asp  Xaa  Leu  Xaa  Xaa  Leu  Asp  Leu  Ser  Pro

145
Gly  Cys    (SEQ ID NO:1)
``` wherein:
Xaa at position 4 is Gln or Glu;
Xaa at position 7 is Gln or Glu;
Xaa at position 22 is Gln, Asn, or Asp;
Xaa at position 27 is Thr or Ala;
Xaa at position 28 is Gln, Glu, or absent;
Xaa at position 34 is Gln or Glu;
Xaa at position 54 is Met, methionine sulfoxide, Leu, Ile, Val, Ala, or Gly;
Xaa at position 56 is Gln or Glu;
Xaa at position 62 is Gln or Glu;
Xaa at position 63 is Gln or Glu;
Xaa at position 68 is Met, methionine sulfoxide, Leu, Ile, Val, Ala, or Gly;
Xaa at position 72 is Gln, Asn, or Asp;
Xaa at position 75 is Gln or Glu;
Xaa at position 78 is Gln, Asn, or Asp;
Xaa at position 82 is Gln, Asn, or Asp;
Xaa at position 100 is Gln, Trp, Tyr, Phe, Ile, Val, or Leu;
Xaa at position 108 is Asp or Glu;
Xaa at position 130 is Gln or Glu;
Xaa at position 134 is Gln or Glu;
Xaa at position 136 is Met, methionine sulfoxide, Leu, Ile, Val, Ala, or Gly;
Xaa at position 138 is Gln, Trp, Tyr, Phe, Ile, Val, or Leu; and
Xaa at position 139 is Gln or Glu.

SEQ ID NO: 2 refers to proteins of the formula:

```
1                   5                        10                       15
Met  Xaa  Val  Pro  Ile  Xaa  Lys  Val  Xaa  Asp  Asp  Thr  Lys  Thr  Leu  Ile 20                       25                       30
Lys  Thr  Ile  Val  Thr  Arg  Ile  Xaa  Asp  Ile  Ser  His  Xaa  Xaa  Ser  Val 35                       40                       45
Ser  Ser  Lys  Xaa  Lys  Val  Thr  Gly  Leu  Asp  Phe  Ile  Pro  Gly  Leu  His 50                       55                       60
Pro  Ile  Leu  Thr  Leu  Ser  Lys  Xaa  Asp  Xaa  Thr  Leu  Ala  Val  Tyr  Xaa 65                       70                       75                       80
Xaa  Ile  Leu  Thr  Ser  Xaa  Pro  Ser  Arg  Xaa  Val  Ile  Xaa  Ile  Ser  Xaa 85                       90                       95
Asp  Leu  Glu  Xaa  Leu  Arg  Asp  Leu  Leu  His  Val  Leu  Ala  Phe  Ser  Lys 100                      105                      110
Ser  Cys  His  Leu  Pro  Xaa  Ala  Ser  Gly  Leu  Glu  Thr  Leu  Xaa  Ser  Leu 115                      120                      125
Gly  Gly  Val  Leu  Glu  Ala  Ser  Gly  Tyr  Ser  Thr  Glu  Val  Val  Ala  Leu 130                      135                      140
Ser  Arg  Leu  Xaa  Gly  Ser  Leu  Xaa  Asp  Xaa  Leu  Xaa  Xaa  Leu  Asp  Leu

145
Ser  Pro  Gly  Cys    (SEQ ID NO:2)
``` wherein:
Xaa at position 2 is any amino acid except Pro;
Xaa at position 6 is Gln or Glu;
Xaa at position 9 is Gln or Glu;
Xaa at position 24 is Gln, Asn, or Asp;
Xaa at position 29 is Thr or Ala;
Xaa at position 30 is Gln, Glu, or absent;
Xaa at position 36 is Gln or Glu;
Xaa at position 56 is Met, methionine sulfoxide, Leu, Ile, Val, Ala, or Gly;
Xaa at position 58 is Gln or Glu;
Xaa at position 64 is Gln or Glu;
Xaa at position 65 is Gln or Glu;
Xaa at position 70 is Met, methionine sulfoxide, Leu, Ile, Val, Ala, or Gly;
Xaa at position 74 is Gln, Asn, or Asp;
Xaa at position 77 is Gln or Glu;
Xaa at position 80 is Gln, Asn, or Asp;
Xaa at position 84 is Gln, Asn, or Asp;
Xaa at position 102 is Gln, Trp, Tyr, Phe, Ile, Val, or Leu;
Xaa at position 110 is Asp or Glu;

Xaa at position 132 is Gln or Glu;

Xaa at position 136 is Gln or Glu;

Xaa at position 138 is Met, methionine sulfoxide, Leu, Ile, Val, Ala, or Gly;

Xaa at position 140 is Gln, Trp, Tyr, Phe, Ile, Val, or Leu; and

Xaa at position 141 is Gln or Glu.

Obesity protein—refers to naturally-occurring obesity proteins.

Obesity protein analog—refers to a protein whose amino acid sequence is, for the most part, the same as that of a naturally-occurring obesity protein, but wherein, at least at one position, the amino acid at that position in the naturally-occurring obesity protein is substituted with a different amino acid, or is deleted. Preferably, the substitutions and deletions are at less than five, and most preferably, less than three positions. Obesity protein analog includes a protein of the Formula (I):

Ser at position 77 is replaced with Ala;

His at position 97 is replaced with Gln, Asn, Ala, Gly, Ser, or Pro;

Trp at position 100 is replaced with Ala, Glu, Asp, Asn, Met, Ser, Thr, or Gly;

Ala at position 101 is replaced with Ser, Asn, Gly, His, Pro, Thr, or Val;

Ser at position 102 is replaced with Arg;

Gly at position 103 is replaced with Ala;

Glu at position 105 is replaced with Gln;

Thr at position 106 is replaced with Lys or Ser;

Leu at position 107 is replaced with Pro;

Gly at position 111 is replaced with Asp;

Gly at position 118 is replaced with Leu;

```
                    5                    10                   15          (I)
  Val Pro Ile Gln Lys Val Gln Asp Asp Thr Lys Thr Leu Ile Lys Thr 20                  25                  30
  Ile Val Thr Arg Ile Asn Asp Ile Ser His Thr Gln Ser Val Ser Ser 35                  40                  45
  Lys Gln Lys Val Thr Gly Leu Asp Phe Ile Pro Gly Leu His Pro Ile 50                  55                  60
  Leu Thr Leu Ser Lys Met Asp Gln Thr Leu Ala Val Tyr Gln Gln Ile 65                  70                  75                  80
  Leu Thr Ser Met Pro Ser Arg Asn Val Ile Gln Ile Ser Asn Asp Leu 85                  90                  95
  Glu Asn Leu Arg Asp Leu Leu His Val Leu Ala Phe Ser Lys Ser Cys 100                 105                 110
  His Leu Pro Trp Ala Ser Gly Leu Glu Thr Leu Asp Ser Leu Gly Gly 115                 120                 125
  Val Leu Glu Ala Ser Gly Tyr Ser Thr Glu Val Val Ala Leu Ser Arg 130                 135                 140
  Leu Gln Gly Ser Leu Gln Asp Met Leu Trp Gln Leu Asp Leu Ser Pro

145
  Gly Cys    (SEQ ID NO:3)
``` wherein:
said protein having at least one of the following substitutions:

Trp at position 138 is replaced with Ala, Glu, Asp, Asn, Met, Ser, Thr, or Gly; and also a protein of the Formula (II):

```
                      5                    10                   15          (II)
  Xaa Xaa Ile Gln Lys Val Gln Asp Asp Thr Lys Thr Leu Ile Lys Thr 20                  25                  30
  Ile Val Thr Arg Ile Xaa Asp Ile Ser His Thr Xaa Ser Val Ser Ser 35                  40                  45
  Lys Gln Lys Val Thr Gly Leu Asp Phe Ile Pro Gly Leu His Pro Ile 50                  55                  60
  Leu Thr Leu Ser Lys Met Asp Gln Thr Leu Ala Val Tyr Gln Gln Ile 65                  70                  75                  80
  Leu Thr Ser Met Pro Ser Arg Xaa Xaa Ile Gln Ile Ser Asn Asp Leu 85                  90                  95
  Glu Asn Leu Arg Asp Leu Leu His Val Leu Ala Phe Ser Lys Ser Cys 100                 105                 110
  His Leu Pro Xaa Ala Ser Gly Leu Glu Thr Leu Asp Ser Leu Gly Gly
```

-continued

```
              115                      120                      125
Val  Leu  Glu  Ala  Ser  Gly  Tyr  Ser  Thr  Glu  Val  Val  Ala  Leu  Ser  Arg 130                      135                      140
Leu  Gln  Gly  Ser  Leu  Gln  Asp  Met  Leu  Xaa  Gln  Leu  Asp  Leu  Ser  Pro

145
Gly  Cys    (SEQ ID NO:4)
``` wherein:
Xaa at position 1 is Val or absent;
Xaa at position 2 is Pro or absent;
Xaa at position 22 is Asn or Ser;
Xaa at position 28 is Gln or absent;
Xaa at position 72 is Asn, Gln, Glu or Asp;
Xaa at position 73 is Val or Met;
Xaa at position 100 is Trp, Gln, Glu, Asp, Ser, Thr, Lys, His, or Arg;
Xaa at position 138 is Trp, Gln, Glu, Asp, Ser, Thr, Lys, His, or Arg;
said protein having at least one of the following substitutions:
  Xaa at position 1 is replaced with Glu, Asp, Ser, Thr, Lys, His, or Arg;
  Xaa at position 2 is replaced with Glu, Asp, Ser, Thr, Lys, His, or Arg;
  Ile at position 3 is replaced with Glu, Asp, Arg, Lys, or His;
  Val at position 30 is replaced with Glu, Asp, Arg, Lys, or His;
  Val at position 36 is replaced with Glu, Asp, Arg, Lys, or His;
  Phe at position 41 is replaced with Glu, Asp, Arg, Lys, or His;
  Ile at position 42 is replaced with Glu, Asp, Arg, Lys, or His;
  Pro at position 43 is replaced with Glu, Asp, Arg, Lys, or His;
  Leu at position 45 is replaced with Glu, Asp, Arg, Lys, or His;
  His at position 46 is replaced with Glu, Asp, Arg, or Lys;
  Pro at position 47 is replaced with Glu, Asp, Arg, Lys, or His;
  Ile at position 48 is replaced with Glu, Asp, Arg, Lys, or His;
  Leu at position 49 is replaced with Glu, Asp, Arg, Lys, or His;
  Thr at position 50 is replaced with Glu, Asp, Arg, Lys, or His;
  Ile at position 74 is replaced with Gln, Glu, Asp, Arg, Lys, His, Thr or Ser;
  Val at position 89 is replaced with Gln, Glu, Asp, Arg, Lys, His, Thr or Ser;
  Phe at position 92 is replaced with Gln, Glu, Asp, Arg, Lys, His, Thr or Ser;
  Pro at position 99 is replaced with Gln, Glu, Asp, Arg, Lys, His, Thr or Ser;
  Leu at position 142 is replaced with Glu, Asp, Arg, Lys, or His;

and also a protein of the Formula (III):

```
                                  5                      10                      15              (III)
       Val  Pro  Ile  Gln  Lys  Val  Gln  Asp  Asp  Thr  Lys  Thr  Leu  Ile  Lys  Thr 20                      25                      30
       Ile  Val  Thr  Arg  Ile  Xaa  Asp  Ile  Ser  His  Thr  Xaa  Ser  Val  Ser  Ser 35                      40                      45
       Lys  Gln  Lys  Val  Thr  Gly  Leu  Asp  Phe  Ile  Pro  Gly  Leu  His  Pro  Ile 50                      55                      60
       Leu  Thr  Leu  Ser  Lys  Met  Asp  Gln  Thr  Leu  Ala  Val  Tyr  Gln  Gln  Ile 65                      70                      75                      80
       Leu  Thr  Ser  Met  Pro  Ser  Arg  Xaa  Xaa  Ile  Gln  Ile  Ser  Asn  Asp  Leu 85                      90                      95
       Glu  Asn  Leu  Arg  Asp  Leu  Leu  His  Val  Leu  Ala  Phe  Ser  Lys  Ser  Cys 100                     105                     110
       His  Leu  Pro  Trp  Ala  Ser  Gly  Leu  Glu  Thr  Leu  Asp  Ser  Leu  Gly  Gly 115                     120                     125
       Val  Leu  Glu  Ala  Ser  Gly  Tyr  Ser  Thr  Glu  Val  Val  Ala  Leu  Ser  Arg 130                     135                     140
       Leu  Gln  Gly  Ser  Leu  Gln  Asp  Met  Leu  Trp  Gln  Leu  Asp  Leu  Ser  Pro

145
       Gly  Cys    (SEQ ID NO:5)
``` wherein:
Xaa at position 22 is Asn or Ser;
Xaa at position 28 is Gln or absent;
Xaa at position 72 in Asn, Gln, Glu, or Asp;

Xaa at position 73 is Val or Met;
said protein having at least one of the following substitutions:

Trp at position 100 is replaced with Glu, Asp, His, Lys, or Arg;

Trp at position 138 is replaced with Glu, Asp, His, Lys, or Arg.

Obesity protein analog precursor—refers to a protein having an even number of amino acids extended from the amino terminus of an obesity protein analog, said even number of amino acids being susceptible to cleavage catalyzed by dDAP to yield an obesity protein analog. dDAP cleaves dipeptides from the amino terminus. It is highly preferred that the second amino acid, that is, the one closer to the carboxy-terminus, in the dipeptides to be cleaved from an obesity protein analog precursor to form an obesity protein analog not be proline.

Support surface—any solid or semi-solid surface or matrix that can be used as is or easily derivatized or activated to bond a protein, exhibits minimal non-specific adsorption, is physically mechanically and chemically stable, is highly porous to provide ligand accessibility, and can be regenerated without deteriorating the surface.

All amino acid abbreviations used in this disclosure are those accepted by the United States Patent and Trademark Office as set forth in 37 C.F.R. §1.822(b)(2) (1990).

As previously stated, one aspect of the present invention is a process wherein an obesity protein analog that is different than a protein of SEQ ID NO:1 is produced by contact between dDAP and an obesity protein analog precursor. In another aspect, the present invention also provides a process for preparing certain obesity protein analogs, which comprises contacting obesity protein analog precursor with dDAP, in the presence of urea. The present invention also provides a process for preparing a protein of SEQ ID NO:1, which comprises contacting a protein of SEQ ID NO:2 with dDAP in the presence of urea under conditions sufficient to allow the action of said dDAP to remove an amino-terminal dipeptide. In the presence of urea, the rate of removal of amino-terminal dipeptides from obesity protein precursor, catalyzed by dDAP, is many-fold higher than in the absence of urea. The higher reaction rate is advantageous because either less enzyme could be used, or the reaction could be carried out in shorter time, resulting in more efficient and less expensive production of obesity protein analog.

Urea, at 4 molar or higher, is often used to terminate reactions catalyzed by enzymes because of its ability to denature enzymes. Indeed, urea was found to inhibit dDAP under certain conditions, as demonstrated by Example 1, below. Thus, in view of the well-known ability of urea to inactivate enzymes, and the data of Example 1, it was unpredictable and unexpected to find that the rate of reaction when dDAP and obesity protein analog precursor were incubated together with urea was actually many-fold higher than the reaction rate in the absence of urea.

The use of the dDAP enzyme to remove dipeptides from proteins of SEQ ID NO:2 in the absence of added urea has a pH optimum of about 2.8, which allows the reaction to be run at acidic pH ranges [U.S. Ser. No. 08/429,362, filed Apr. 26, 1995]. The advantages of an acidic pH reaction may include less formation of interchain disulfide dimers or polymers and less oxidation of methionine residues. Quite unpredictably, it was discovered that the pH optimum of the conversion reaction carried out according to the present invention is markedly shifted toward a more neutral, but still slightly acidic pH, as described in Example 2, below.

The dDAP enzyme employed in the present process is obtained by fermentation of *D. discoideum* Ax3 (ATCC 28368). The dDAP enzyme may be purified prior to use in the present process, for example, by centrifugation, anion exchange chromatography, hydrophobic interaction chromatography and size exclusion chromatography, to yield a highly purified solution of dDAP enzyme which can be stored or used immediately. Methods of making and using dDAP for removing N-terminal dipeptides from certain precursor polypeptides have been disclosed and claimed in U.S. Pat. Nos. 5,565,330, 5,565,349, and 5,573,923, and in U.S. Ser. No. 08/429,362. The entire teaching of each of the four documents is incorporated herein by reference. The preparation of dDAP, the conduct of dDAP assays, the definition of activity units, and a preliminary characterization of dDAP are described in Atkinson, et al., *Biochemistry* 34:10827–10834 (1995).

This invention may also be carried out by immobilizing dDAP onto a support surface, and used in plug-flow reactors and batch reactors, as described in Example 7, below. Other methods for immobilizing dDAP onto a support surface are disclosed in U.S. Pat. No. 5,573,923. Solid support surfaces include, without limitation, inorganic materials, such as, porous silica, controlled pore glass, and hydroxyapatite, synthetic organic polymers, such as, polyacrylamide, polymethacrylate, and polystyrene, polysaccharides, such as, cellulose, dextran, Sephadex®, Sepharose®, and agarose, and membranous support surfaces, such as, cross-flow membranes and hollow fiber membranes. An example of a commercially available membrane is the Acti-Mod® quaternary amine module (FMC BioProducts).

Preferred support surfaces are those that do not adversely affect dDAP once bound to the surface. Commercially-available polysaccharide matrices formed into various sized beads are more preferred because they are porous, easy to handle, and are well known and understood in the biochemical purification art. More highly preferred support surfaces are commercially-available anion exchange resins. The most preferred support surface is Q Sepharose® resin (Pharmacia). See *Affinity Chromatography Principles & Methods*, Pharmacia Fine Chemicals, (1983); *Biotechnology Products Catalog* 1993, Pharmacia Biotech Inc, 800 Centennial Ave., Piscataway, N.J. 08854.

Enzyme immobilization is most usually accomplished using solid supports, generally chromatography resins, that have been modified or activated to include functional groups that permit the covalent coupling of resin to enzyme. Typically, aliphatic linker arms are employed. An example of a commercially available covalent immobilization resin is Activated CH Sepharose® 4B (Pharmacia). It is one of many chemistries that Pharmacia has attached to the Sepharose® 4B base matrix. In general, activated resins cost significantly more than anion exchange resins of the same base matrix, are not available in as wide of a variety of base matrix types as ion exchange chromatographic media and may therefore be more limited in their ability to handle low clarity column charges or high mobile phase flow rates.

The dDAP enzyme may also be noncovalently attached to a solid support surface, through, for example, ionic or hydrophobic mechanisms. A large variety of ion exchange and hydrophobic interaction chromatography resins are available from a large number of commercial sources, at lower cost than the activated, covalent immobilization resins. Immobilization of dDAP on chromatography resin, for use in a packed bed (plug-flow) reactor configuration, may be accomplished by employing any of a variety of loading strategies. For example, the enzyme may be loaded onto the resin by direct charge, wherein the resin is packed into a column and then a solution of dDAP is passed through the packed bed under conditions to cause adherence of dDAP. Alternatively, a reslurried packed bed may be produced by first immobilizing dDAP using the direct charge strategy, then resuspending the resin having dDAP immobilized on it, and finally repacking the resin. In yet another approach, referred to as batch-loaded, dDAP is immobilized on resin that is in suspension. After immobilization, the resin is then packed into a column to carry out the reaction. Of the mentioned loading strategies, the batch-loaded method is preferred for preparing a packed bed of immobilized dDAP.

The above discussion is in no way meant to limit the scope of the invention. The ordinarily skilled artisan will know numerous other schemes for linking proteins to support surfaces. Moreover, the choice of support surface and the method of immobilizing dDAP is largely a matter of convenience and depends on the practitioner's familiarity with, and preference for, various supports surfaces, as well as his preference for various immobilizing schemes, and knowledge of the substrate.

The obesity protein precursor used in the present invention can be prepared by any of a variety of recognized peptide synthesis techniques including classical (solution) methods, solid phase methods, semi-synthetic methods, and more recent recombinant DNA methods. Recombinant methods are preferred if a large mass of obesity protein analog is required. Obesity protein analog precursor is preferably prepared by techniques essentially as taught in WO 96/23515, WO 96/23517, EP 0743321, published Nov. 20, 1996, U.S. Ser. No. 60/000451, filed Jun. 22, 1996, and U.S. Ser. No. 08/429,362. The entire teaching of each of the five aforementioned documents that is applicable to the biosynthesis and purification of obesity protein analog precursors using recombinant DNA methods is incorporated expressly herein by reference. The skilled artisan will know how to apply the teachings of the mentioned references to make any obesity protein analog precursor for use in the present invention. When urea is used in the present process, the obesity protein analog precursor is not necessarily properly renatured.

Recombinant methods are preferred if a high yield is desired. The basic steps in the recombinant production of protein include:

a) construction of a synthetic or semi-synthetic (or isolation from natural sources) DNA encoding the protein, b) integrating the coding sequence into an expression vector in a manner suitable for the expression of the protein either alone or as a fusion protein, c) transforming an appropriate eukaryotic or prokaryotic host cell with the expression vector, d) growing the transformed host cell under conditions permitting the expression of the recombinant protein, and e) recovering and purifying the recombinantly produced protein.

Synthetic genes, the in vitro or in vivo transcription and translation of which will result in the production of the protein may be constructed by techniques well known in the art. Owing to the natural degeneracy of the genetic code, the skilled artisan will recognize that a sizable yet definite number of DNA sequences may be constructed which encode the proteins. Techniques for making substitutional mutations at predetermined sites in DNA having a known sequence are well known, for example M13 primer mutagenesis. The mutations that might be made in the DNA encoding the obesity protein analog precursors used in the instant process must not place the sequence out of reading frame and preferably will not create complementary regions that could produce secondary mRNA structure. See DeBoer et al., EP 75,444A (1983).

Methodology of synthetic gene construction is well known in the art. For example, see Brown, et al. (1979) Methods in Enzymology, Academic Press, N.Y., Vol. 68, pgs. 109–151. The DNA sequence corresponding to the synthetic protein gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

The gene encoding the protein may also be created by using polymerase chain reaction (PCR). The template can be a cDNA library (commercially available from CLONETECH or STRATAGENE) or mRNA isolated from human adipose tissue. Such methodologies are well known in the art Maniatis, et al. *Molecular Cloning: A Laboratory Manual*, Cold Spring Harbor Press, Cold Spring Harbor Laboratory, Cold Spring Harbor, N.Y. (1989).

Construction of suitable vectors containing the desired coding and control sequences employ standard ligation techniques. Isolated plasmids or DNA fragments are cleaved, tailored, and religated in the form desired to form the plasmids required.

To effect the translation of the desired protein, one inserts the engineered synthetic DNA sequence in any of a plethora of appropriate recombinant DNA expression vectors through the use of appropriate restriction endonucleases. A synthetic coding sequence is designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the protein.

In general, plasmid vectors containing promoters and control sequences that are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., *Gene* 2: 95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein incorporated by reference. The gene encoding A-C-B proinsulin described in U.S. Pat. No. 5,304,493 can be removed from the plasmid pRB182 with restriction enzymes NdeI and BamHI. The genes encoding the protein of the present invention can be inserted into the plasmid backbone on a NdeI/BamHI restriction fragment cassette.

In general, procaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Prokaryotes also are used for expression. The aforementioned strains, as well as *E. coli* W3110 (prototrophic, ATCC No. 27325), bacilli such as *Bacillus subtilis*, and other enterobacteriaceae such as *Salmonella typhimurium* or *Serratia marcescans*, and various *Pseudomonas* species may be used. Promoters suitable for use with prokaryotic hosts include the β-lactamase (vector pGX2907 [ATCC 39344] contains the replicon and β-lactamase gene) and lactose promoter systems (Chang et al., *Nature*, 275:615 (1978); and Goeddel et al., *Nature* 281:544 (1979)), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

Urea suitable for use in the present process in commercially available in large quantities, and preferably is deionized and stabilized to control formation of ionic species that may adversely react with any of the proteins involved in the conversion reaction.

The reader will appreciate that the present invention may be practiced with a wide variety of reactor configurations, temperatures, pH ranges, enzyme to precursor ratios, precursor concentrations, urea concentrations, conductivities, and time periods. Discussion of some of these aspects is presented so that the reader will understand that the invention is not limited to the conditions set forth in the examples herein.

Any of a number of reactor configurations known in the art may be employed advantageously to carry out the present process. For example, without limitation, the invention may be carried out in a batch reactor, a fed-batch reactor, a continuously-fed tank reactor, or a plug-flow reactor. Particularly preferred are the batch reactor and plug-flow reactor configurations. In any of the reactor configurations, the dDAP enzyme may be free in solution or immobilized on a support surface.

The temperature during contact between the obesity protein analog precursor and dDAP is between about 2° C. and about 45° C. More preferably, the temperature is between about 2° C. and about 37°0 C., and most preferably between about 20° C. and about 37° C.

Contact between the obesity protein analog precursor and dDAP generally occurs in an aqueous medium that is suitably buffered to maintain the pH. When urea is present in the aqueous medium, then the pH is preferably between about 4.0 and about 7.0, more preferably, between about pH 4.0 and about 6.0, and, most preferably, between about pH 4.5 and about pH 5.5. In the absence of urea, the pH is preferably between about 2.0 and about 5.5, more preferably from about 2.4 to about 4.5, and most preferably from about 2.4 to about 3.2. Any of a wide range of buffering agents can be employed to control the pH during contact. The only requirements for the buffering agent or agents are ability to maintain pH close to the selected pH value and lack of interference with the reaction. The skilled artisan wishing to carry out the instant invention will be able to select an appropriate buffering compound relying on knowledge generally available in the art.

For reactor configurations such as the batch reactor, the length of time required to achieve a desired percent conversion will be affected by the activity of dDAP used relative to the amount of precursor sought to be converted. The ratio of dDAP to precursor is preferably from about 0.005 U/gram to about 10 U/gram. More preferably, the ratio is less than about 2 U/gram. Most preferably, the ratio is less than about 0.5 U/gram.

For immobilized dDAP, the reaction time or residence time required to achieve a desired conversion will be affected by the concentration of dDAP on the solid support. For dDAP immobilized on chromatography resin, the preferred concentration of dDAP on the solid support is in the range of 1 U/liter to 20,000 U/liter. More preferred is a concentration of 100 U/liter to 10,000 U/liter. Most preferred is a concentration between 500 U/liter and 5,000 U/liter. The skilled artisan will be cognizant of the interplay of enzyme and precursor concentration, flow rate, residence time, and temperature, among other variables, and is able to adjust the mentioned variables appropriately to achieve a desired conversion percentage.

The length of time required to achieve a desired percent conversion will also be affected by the concentration of precursor used in the conversion reaction. The precursor concentration is preferably between about 0.5 mg/mL and 100 mg/mL, more preferably, between about 1 mg/mL and about 50 mg/mL, and most preferably between about 2 mg/mL and about 20 mg/mL. Other preferred ranges of precursor concentrations are from about 0.5 mg/mL to about 25 mg/mL, from about 1 mg/mL to about 5 mg/mL, and from about 2 mg/mL to about 25 mg/mL.

Contact between obesity protein analog precursor and dDAP can be for any given time period, ranging from only a few seconds to several days. Preferably, the contact is from between about 1 minute to about 24 hours, and most preferably, from about 1 hour to about 8 hours. The skilled artisan will recognize that the time of contact varies with the particular conditions employed. Contact time is applicable to both batch and plug-flow reactor configurations.

If immobilized dDAP is employed in the process, then, once dDAP has been immobilized onto a support surface, conversion of obesity protein analog precursor to processed obesity protein analog can be accomplished under a variety of conditions. The preferred way is to pack a chromatography column with immobilized dDAP so that the precursor substrate can be contacted with the immobilized enzyme by passing a solution of precursor dissolved in urea through the bed. Because the enzyme remains attached to the support surface, it does not become physically part of the reactant mixture and can therefore be reused. The contacting step is preferably repeated one or more times to ensure complete processing of the protein. Thus, the reactant/product stream may be recycled over the same dDAP bed one or more times or may be sequentially passed over separate dDAP beds.

Preferred obesity protein analogs produced by the present process are those of the Formula (I), (II) or (III). More preferred proteins produced by the present invention include the proteins of Formula (II) or (III). Further preferred obesity protein analogs produced by the present process are those of SEQ ID NO:6 through 16:

```
                    5                   10                  15
Val Pro Ile Gln Lys Val Gln Asp Asp Thr Lys Thr Leu Ile Lys Thr
            20                  25                  30
Ile Val Thr Arg Ile Asn Asp Ile Ser His Thr Gln Ser Val Ser Ser
        35                  40                  45
Lys Gln Lys Val Thr Gly Leu Asp Phe Ile Pro Gly Leu His Pro Ile
    50                  55                  60
Leu Thr Leu Ser Lys Met Asp Gln Thr Leu Ala Val Tyr Gln Gln Ile
65                  70                  75                  80
Leu Thr Ser Met Pro Ser Arg Asn Val Ile Gln Ile Ser Asn Asp Leu
                85                  90                  95
Glu Asn Leu Arg Asp Leu Leu His Val Leu Ala Phe Ser Lys Ser Cys
            100                 105                 110
His Leu Pro Ala Ala Ser Gly Leu Glu Thr Leu Asp Ser Leu Gly Gly
        115                 120                 125
Val Leu Glu Ala Ser Gly Tyr Ser Thr Glu Val Val Ala Leu Ser Arg
    130                 135                 140
Leu Gln Gly Ser Leu Gln Asp Met Leu Trp Gln Leu Asp Leu Ser Pro
145
Gly Cys       (SEQ ID NO:6)
                    5                   10                  15
Val Pro Ile Gln Lys Val Gln Asp Asp Thr Lys Thr Leu Ile Lys Thr
            20                  25                  30
Ile Val Thr Arg Ile Asn Asp Ile Ser His Thr Gln Ser Val Ser Ser
        35                  40                  45
Lys Gln Lys Val Thr Gly Leu Asp Phe Ile Pro Gly Leu His Pro Asp
    50                  55                  60
Leu Thr Leu Ser Lys Met Asp Gln Thr Leu Ala Val Tyr Gln Gln Ile
65                  70                  75                  80
Leu Thr Ser Met Pro Ser Arg Asn Val Ile Gln Ile Ser Asn Asp Leu
                85                  90                  95
Glu Asn Leu Arg Asp Leu Leu His Val Leu Ala Phe Ser Lys Ser Cys
            100                 105                 110
His Leu Pro Gln Ala Ser Gly Leu Glu Thr Leu Asp Ser Leu Gly Gly
        115                 120                 125
Val Leu Glu Ala Ser Gly Tyr Ser Thr Glu Val Val Ala Leu Ser Arg
    130                 135                 140
Leu Gln Gly Ser Leu Gln Asp Met Leu Trp Gln Leu Asp Leu Ser Pro
145
Gly Cys       (SEQ ID NO:7)
                    5                   10                  15
Val Pro Ile Gln Lys Val Gln Asp Asp Thr Lys Thr Leu Ile Lys Thr
            20                  25                  30
Ile Val Thr Arg Ile Asn Asp Ile Ser His Thr Gln Ser Val Ser Ser
        35                  40                  45
Lys Gln Lys Val Thr Gly Leu Asp Phe Ile Pro Gly Leu His Pro Ile
    50                  55                  60
Leu Thr Leu Ser Lys Met Asp Gln Thr Leu Ala Val Tyr Gln Gln Ile
65                  70                  75                  80
Leu Thr Ser Met Pro Ser Arg Asn Val Ile Gln Ile Ser Asn Asp Leu
                85                  90                  95
Glu Asn Leu Arg Asp Leu Leu His Val Leu Ala Phe Ser Lys Ser Cys
            100                 105                 110
His Leu Pro Asp Ala Ser Gly Leu Glu Thr Leu Asp Ser Leu Gly Gly
```

```
                115                     120                     125
Val Leu Glu Ala Ser Gly Tyr Ser Thr Glu Val Val Ala Leu Ser Arg
        130                     135                     140
Leu Gln Gly Ser Leu Gln Asp Met Leu Trp Gln Leu Asp Leu Ser Pro
145
Gly Cys     (SEQ ID NO:8)
                     5                      10                      15
Val Pro Ile Gln Lys Val Gln Asp Asp Thr Lys Thr Leu Ile Lys Thr
            20                      25                      30
Ile Val Thr Arg Ile Asn Asp Ile Ser His Thr Gln Ser Val Ser Ser
        35                      40                      45
Lys Gln Lys Val Thr Gly Leu Asp Phe Ile Pro Gly Leu His Pro Ile
    50                      55                      60
Leu Thr Leu Ser Lys Met Asp Gln Thr Leu Ala Val Tyr Gln Gln Ile
65                      70                      75                      80
Leu Thr Ser Met Pro Ser Arg Asn Val Ile Gln Ile Ser Asn Asp Leu
                85                      90                      95
Glu Asn Leu Arg Asp Leu Leu His Val Leu Ala Phe Ser Lys Ser Cys
            100                     105                     110
His Leu Pro Glu Ala Ser Gly Leu Glu Thr Leu Asp Ser Leu Gly Gly
        115                     120                     125
Val Leu Glu Ala Ser Gly Tyr Ser Thr Glu Val Val Ala Leu Ser Arg
        130                     135                     140
Leu Gln Gly Ser Leu Gln Asp Met Leu Trp Gln Leu Asp Leu Ser Pro
145
Gly Cys     (SEQ ID NO:9)
                     5                      10                      15
Val Pro Ile Gln Lys Val Gln Asp Asp Thr Lys Thr Leu Ile Lys Thr
            20                      25                      30
Ile Val Thr Arg Ile Asn Asp Ile Ser His Thr Gln Ser Val Ser Ser
        35                      40                      45
Lys Gln Lys Val Thr Gly Leu Asp Phe Ile Pro Gly Leu His Pro Asp
    50                      55                      60
Leu Thr Leu Ser Lys Met Asp Gln Thr Leu Ala Val Tyr Gln Gln Ile
65                      70                      75                      80
Leu Thr Ser Met Pro Ser Arg Asn Val Ile Gln Ile Ser Asn Asp Leu
                85                      90                      95
Glu Asn Leu Arg Asp Leu Leu His Val Leu Ala Phe Ser Lys Ser Cys
            100                     105                     110
His Leu Pro Asp Ala Ser Gly Leu Glu Thr Leu Asp Ser Leu Gly Gly
        115                     120                     125
Val Leu Glu Ala Ser Gly Tyr Ser Thr Glu Val Val Ala Leu Ser Arg
        130                     135                     140
Leu Gln Gly Ser Leu Gln Asp Met Leu Trp Gln Leu Asp Leu Ser Pro
145
Gly Cys     (SEQ ID NO:10)
                     5                      10                      15
Val Pro Ile Gln Lys Val Gln Asp Asp Thr Lys Thr Leu Ile Lys Thr
            20                      25                      30
Ile Val Thr Arg Ile Asp Asp Ile Ser His Thr Gln Ser Val Ser Ser
        35                      40                      45
Lys Gln Lys Val Thr Gly Leu Asp Phe Ile Pro Gly Leu His Pro Ile
    50                      55                      60
Leu Thr Leu Ser Lys Met Asp Gln Thr Leu Ala Val Tyr Gln Gln Ile
65                      70                      75                      80
Leu Thr Ser Met Pro Ser Arg Asn Val Ile Gln Ile Ser Asn Asp Leu
```

```
                    85                      90                       95
Glu Asn Leu Arg Asp Leu Leu His Val Leu Ala Phe Ser Lys Ser Cys 100                     105                      110
His Leu Pro Trp Ala Ser Gly Leu Glu Thr Leu Asp Ser Leu Gly Gly 115                     120                      125
Val Leu Glu Ala Ser Gly Tyr Ser Thr Glu Val Val Ala Leu Ser Arg 130                     135                      140
Leu Gln Gly Ser Leu Gln Asp Met Leu Trp Gln Leu Asp Leu Ser Pro

145
Gly Cys     (SEQ ID NO:11)
```

```
                     5                      10                       15
Val Pro Ile Gln Lys Val Gln Asp Asp Thr Lys Thr Leu Ile Lys Thr 20                      25                       30
Ile Val Thr Arg Ile Asn Asp Ile Ser His Ala Gln Ser Val Ser Ser 35                      40                       45
Lys Gln Lys Val Thr Gly Leu Asp Phe Ile Pro Gly Leu His Pro Ile 50                      55                       60
Leu Thr Leu Ser Lys Met Asp Gln Thr Leu Ala Val Tyr Gln Gln Ile 65                      70                      75                   80
Leu Thr Ser Met Pro Ser Arg Asn Val Ile Gln Ile Ser Asn Asp Leu 85                      90                       95
Glu Asn Leu Arg Asp Leu Leu His Val Leu Ala Phe Ser Lys Ser Cys 100                     105                      110
His Leu Pro Trp Ala Ser Gly Leu Glu Thr Leu Asp Ser Leu Gly Gly 115                     120                      125
Val Leu Glu Ala Ser Gly Tyr Ser Thr Glu Val Val Ala Leu Ser Arg 130                     135                      140
Leu Gln Gly Ser Leu Gln Asp Met Leu Trp Gln Leu Asp Leu Ser Pro

145
Gly Cys     (SEQ ID NO:12)
```

```
                     5                      10                       15
Val Pro Ile Gln Lys Val Gln Asp Asp Thr Lys Thr Leu Ile Lys Thr 20                      25                       30
Ile Val Thr Arg Ile Asn Asp Ile Ser His Thr Gln Ser Val Ser Ser 35                      40                       45
Lys Gln Lys Val Thr Gly Leu Asp Phe Ile Pro Gly Leu His Pro Ile 50                      55                       60
Leu Thr Leu Ser Lys Met Asp Gln Thr Leu Ala Val Tyr Gln Gln Ile 65                      70                      75                   80
Leu Thr Ser Met Pro Ser Arg Asn Val Ile Gln Ile Ser Asn Asp Leu 85                      90                       95
Glu Asn Leu Arg Asp Leu Leu His Val Leu Ala Phe Ser Lys Ser Cys 100                     105                      110
His Leu Pro Trp Ala Ser Gly Leu Glu Thr Leu Asp Ser Leu Gly Gly 115                     120                      125
Val Leu Glu Ala Ser Gly Tyr Ser Thr Glu Val Val Ala Leu Ser Arg 130                     135                      140
Leu Gln Gly Ser Leu Gln Asp Met Leu Gln Gln Leu Asp Leu Ser Pro

145
Gly Cys     (SEQ ID NO:13)
```

```
                     5                      10                       15
Val Pro Ile Gln Lys Val Gln Asp Asp Thr Lys Thr Leu Ile Lys Thr 20                      25                       30
Ile Val Thr Arg Ile Asn Asp Ile Ser His Thr Gln Ser Val Ser Ser 35                      40                       45
Lys Gln Lys Val Thr Gly Leu Asp Phe Ile Pro Gly Leu His Pro Ile
```

```
                    50                      55                      60
Leu Thr Leu Ser Lys Met Asp Gln Thr Leu Ala Val Tyr Gln Gln Ile
65                      70                      75                      80
Leu Thr Ser Met Pro Ser Arg Asn Val Ile Gln Ile Ser Asn Asp Leu
                    85                      90                      95
Glu Asn Leu Arg Asp Leu Leu His Val Leu Ala Phe Ser Lys Ser Cys
                   100                     105                     110
His Leu Pro Gln Ala Ser Gly Leu Glu Thr Leu Asp Ser Leu Gly Gly
                115                     120                     125
Val Leu Glu Ala Ser Gly Tyr Ser Thr Glu Val Val Ala Leu Ser Arg
           130                     135                     140
Leu Gln Gly Ser Leu Gln Asp Met Leu Gln Gln Leu Asp Leu Ser Pro
145
Gly Cys     (SEQ ID NO:14)

5                      10                      15
Val Pro Ile Gln Lys Val Gln Asp Asp Thr Lys Thr Leu Ile Lys Thr
                20                      25                      30
Ile Val Thr Arg Ile Asn Asp Ile Ser His Thr Gln Ser Val Ser Ser
           35                      40                      45
Lys Gln Lys Val Thr Gly Leu Asp Phe Ile Pro Gly Leu His Pro Ile
        50                      55                      60
Leu Thr Leu Ser Lys Met Asp Gln Thr Leu Ala Val Tyr Gln Gln Ile
65                      70                      75                      80
Leu Thr Ser Met Pro Ser Arg Asn Val Ile Gln Ile Ser Asn Asp Leu
                    85                      90                      95
Glu Asn Leu Arg Asp Leu Leu His Val Leu Ala Phe Ser Lys Ser Cys
                   100                     105                     110
His Leu Pro Ala Ala Ser Gly Leu Glu Thr Leu Asp Ser Leu Gly Gly
                115                     120                     125
Val Leu Glu Ala Ser Gly Tyr Ser Thr Glu Val Val Ala Leu Ser Arg
           130                     135                     140
Leu Gln Gly Ser Leu Gln Asp Met Leu Gln Gln Leu Asp Leu Ser Pro
145
Gly Cys     (SEQ ID NO:15)

5                      10                      15
Val Pro Ile Gln Lys Val Gln Asp Asp Thr Lys Thr Leu Ile Lys Thr
                20                      25                      30
Ile Val Thr Arg Ile Asn Asp Ile Ser His Thr Gln Ser Val Ser Ser
           35                      40                      45
Lys Gln Lys Val Thr Gly Leu Asp Phe Ile Pro Gly Leu His Pro Ile
        50                      55                      60
Leu Thr Leu Ser Lys Met Asp Gln Thr Leu Ala Val Tyr Gln Gln Ile
65                      70                      75                      80
Leu Thr Ser Met Pro Ser Arg Asp Val Ile Gln Ile Ser Asn Asp Leu
                    85                      90                      95
Glu Asn Leu Arg Asp Leu Leu His Val Leu Ala Phe Ser Lys Ser Cys
                   100                     105                     110
His Leu Pro Asp Ala Ser Gly Leu Glu Thr Leu Asp Ser Leu Gly Gly
                115                     120                     125
Val Leu Glu Ala Ser Gly Tyr Ser Thr Glu Val Val Ala Leu Ser Arg
           130                     135                     140
Leu Gln Gly Ser Leu Gln Asp Met Leu Trp Gln Leu Asp Leu Ser Pro
145
Gly Cys     (SEQ ID NO:16)
```

Other preferred embodiments of the present process comprise contacting a protein of SEQ ID NO:2 wherein Xaa at position 2 is Arg, Asp, or Tyr with dDAP in the presence of urea. Yet other preferred embodiments comprise contacting proteins of SEQ ID NO:2 wherein:

Xaa at position 6 is Gln;
Xaa at position 9 is Gln;
Xaa at position 24 is Asn or Asp;
Xaa at position 29 is Thr or Ala;
Xaa at position 30 is Gln or absent;
Xaa at position 36 is Gln;
Xaa at position 56 is Met;
Xaa at position 58 is Gln;
Xaa at position 64 is Gln;
Xaa at position 65 is Gln;
Xaa at position 70 is Met;
Xaa at position 74 is Asn;
Xaa at position 77 is Gln;
Xaa at position 80 is Asn;
Xaa at position 84 is Asn;
Xaa at position 102 is Trp;
Xaa at position 110 is Asp;
Xaa at position 132 is Gln;
Xaa at position 136 is Gln;
Xaa at position 138 is Met;
Xaa at position 140 is Trp; and
Xaa at position 141 is Gln.

The obesity protein analog precursor used in the present process has an even number of amino acids extended from the amino terminus of an obesity protein analog, said even number of amino acids being susceptible to cleavage catalyzed by dDAP to yield intact obesity protein analog. Preferably, the number of amino acids extended from the amino terminus of an obesity protein analog precursor is 2; that is, the precursor has a dipeptide attached to the amino terminus of an obesity protein analog. Preferred dipeptides extended from the amino terminus of an obesity protein analog in the precursor used in the present invention have the sequences Met-Xaa, wherein Xaa is any amino acid, except proline. More highly preferred dipeptides extended from the amino terminus of an obesity protein analog are Met-Arg, Met-Tyr, and Met-Asp. The most preferred dipeptide extended from the amino terminus of an obesity protein analog is Met-Arg. A preferred obesity protein analog precursor is the protein of SEQ ID NO:17:

```
                    5                  10                 15
Met Arg Val Pro Ile Gln Lys Val Gln Asp Asp Thr Lys Thr Leu Ile 20                  25                 30
Lys Thr Ile Val Thr Arg Ile Asn Asp Ile Ser His Thr Gln Ser Val 35                  40                 45
Ser Ser Lys Gln Lys Val Thr Gly Leu Asp Phe Ile Pro Gly Leu His 50                  55                 60
Pro Ile Leu Thr Leu Ser Lys Met Asp Gln Thr Leu Ala Val Tyr Gln 65                  70                  75                 80
Gln Ile Leu Thr Ser Met Pro Ser Arg Asn Val Ile Gln Ile Ser Asn 85                  90                 95
Asp Leu Glu Asn Leu Arg Asp Leu Leu His Val Leu Ala Phe Ser Lys 100                 105                110
Ser Cys His Leu Pro Ala Ala Ser Gly Leu Glu Thr Leu Asp Ser Leu 115                 120                125
Gly Gly Val Leu Glu Ala Ser Gly Tyr Ser Thr Glu Val Val Ala Leu 130                 135                 140
Ser Arg Leu Gln Gly Ser Leu Gln Asp Met Leu Trp Gln Leu Asp Leu

145
Ser Pro Gly Cys   (SEQ ID NO:17)
```

The following preparations and examples are presented to further illustrate the present invention. The scope of the present invention is not to be construed as merely consisting of the following preparation and examples.

Preparation 1

A DNA sequence encoding the following protein sequence:

```
 1                  5                  10                 15
Met Arg Val Pro Ile Gln Lys Val Gln Asp Asp Thr Lys Thr Leu Ile 20                  25                 30
Lys Thr Ile Val Thr Arg Ile Asn Asp Ile Ser His Thr Gln Ser Val 35                  40                 45
Ser Ser Lys Gln Lys Val Thr Gly Leu Asp Phe Ile Pro Gly Leu His
```

-continued

```
             50                      55                      60
Pro  Ile  Leu  Thr  Leu  Ser  Lys  Met  Asp  Gln  Thr  Leu  Ala  Val  Tyr  Gln 65                      70                      75                      80
Gln  Ile  Leu  Thr  Ser  Met  Pro  Ser  Arg  Asn  Val  Ile  Gln  Ile  Ser  Asn 85                      90                      95
Asp  Leu  Glu  Asn  Leu  Arg  Asp  Leu  Leu  His  Val  Leu  Ala  Phe  Ser  Lys 100                     105                     110
Ser  Cys  His  Leu  Pro  Trp  Ala  Ser  Gly  Leu  Glu  Thr  Leu  Asp  Ser  Leu 115                     120                     125
Gly  Gly  Val  Leu  Glu  Ala  Ser  Gly  Tyr  Ser  Thr  Glu  Val  Val  Ala  Leu 130                     135                     140
Ser  Arg  Leu  Gln  Gly  Ser  Leu  Gln  Asp  Met  Leu  Trp  Gln  Leu  Asp  Leu

145
Ser  Pro  Gly  Cys   (SEQ ID NO:18)
``` is obtained using standard PCR methodology. A forward primer (5'-GG GG CAT ATG AGG GTA CCT ATC CAG AAA GTC CAG GAT GAC AC) and a reverse primer (5'-GG GG GGATC CTA TTA GCA CCC GGG AGA CAG GTC CAG CTG CCA CAA CAT) are used to amplify sequences from a human fat cell library (commercially available from CLONETECH). The PCR product is cloned into PCR-Script (available from STRATAGENE) and sequenced.

Preparation 2

Vector Construction

A plasmid containing the DNA sequence encoding the protein of Preparation 1 is constructed to include NdeI and BamHI restriction sites. The plasmid carrying the cloned PCR product is digested with NdeI and BamHI restriction enzymes. The small ~ 450bp fragment is gel-purified and ligated into the vector pRB182 from which the coding sequence for A-C-B proinsulin is deleted. The ligation products are transformed into E. coli DH10B (commercially available from GIBCO-BRL) and colonies growing on tryptone-yeast (DIFCO) plates supplemented with 10 mg/mL of tetracycline are analyzed. Plasmid DNA is isolated, digested with NdeI and BamHI and the resulting fragments are separated by agarose gel electrophoresis. Plasmids containing the expected ~ 450bp NdeI to BamHI fragment are kept. E. coli B BL21 (DE3) (commercially available from NOVOGEN) are transformed with this second plasmid expression suitable for culture for protein production.

Preparation 3

Preparation of an Obesity Protein Analog Precursor

The teachings of U.S. Ser. No. 08/429,362 were essentially followed in order to express in recombinant E. coli the obesity protein analog having the sequence SEQ ID NO:17 and to purify said expressed precursor. The entire teaching of U.S. Ser. No. 08/429;362 dealing with expression and purification of obesity protein analog precursors is hereby expressly incorporated by reference.

Preparation 4

Preparation of dDAP dDAP was prepared essentially as taught in Examples 1 and 2 of U.S. Pat. Nos. 5,565,330, 5,565,349, and 5,573,923.

EXAMPLE 1

Effect of Urea on dDAP Activity Toward GFpNA

Samples of dDAP were incubated for one hour at 25° C. in the presence of either 2 molar urea or 6.3 molar urea. After this incubation, only 43% and 0.5% of the original dDAP activity remained, respectively. A dDAP sample to which no urea had been added retained 100% of the initial activity. In this experiment, dDAP activity was measured using the substrate, GFpNA, in a spectrophotometric assay, essentially as described in Atkinson, et al, *Biochemistry* 34:10827–10834 (1995).

EXAMPLE 2

Effect of pH and Urea on dDAP Activity

An obesity protein analog precursor (SEQ ID NO:17, 1.7 mg/mL) was contacted with dDAP (10 U/gram of precursor) for 30 minutes at 24° C. at various pH levels that were controlled by the mixed buffer system of Tris (25 mM) and citrate acid (25 mM). Urea (8.5 molar) was added to some reaction mixtures to give a final urea concentration of 5.8 molar. The concentration of the product, obesity protein analog (SEQ ID NO:6), was measured by reverse-phase HPLC (Table 1).

TABLE 1

Effect of pH and Urea on dDAP-Catalyzed Conversion of Precursor to Obesity Protein Analog

| | % of Precursor Converted to Obesity Protein Analog in 30 Minutes at 24° C. | |
|---|---|---|
| pH | No Urea | 5.8 molar Urea |
| 2.7 | 50 | 8 |
| 3.2 | 55 | 13 |
| 3.4 | 55 | 15 |
| 3.5 | 46 | 20 |
| 3.9 | 39 | 60 |
| 4.2 | 38 | 80 |
| 5.6 | | 90 |
| 7.8 | | 9 |
| 9.8 | | 8 |

The data in Table 1 demonstrate that urea at 5.8 molar causes a dramatic shift in the optimum pH for the conversion reaction, from the moderately acidic (about pH 3), without urea, to the slightly acidic (about pH 5), with urea.

EXAMPLE 3

Effect of pH and Urea on dDAP Activity

The optimum pH, urea concentration, and conductivity were estimated by carrying out a three-factor response surface design experiment. An obesity protein analog precursor (SEQ ID NO:17, 0.79 mg/mL) was contacted with dDAP (2 U/gram of precursor) for 30 minutes at 24° C. at various pH levels (3, 5, and 7), in various concentrations of urea (3.5, 5.3, and 7 molar), and at various conductivities (2.5, 10.8, and 19 mS). From this multi-factor experiment, the optimum conditions for contacting obesity protein analog precursor and dDAP were found to be 6 molar urea and pH 5.0. Reaction rate had only a weak, inverse relationship with conductivity.

EXAMPLE 4

Reaction of a Mixed Disulfide Precursor in the Presence of Urea

In the presence of urea, the process of the present invention is relatively unaffected by whether the precursor has its intramolecular disulfide bond. A form of an obesity protein analog precursor that did not have an intact disulfide bond was prepared by exposing an analog precursor (SEQ ID NO:17) having the intramolecular disulfide bond to 5 mM cysteine and 7 molar urea at pH 8.3 to form the cysteinyl-mixed disulfide precursor. Then, said mixed disulfide precursor (4.6 mg/mL) was contacted with dDAP at 24° C. and pH 5 in 40 mM citrate buffer containing urea at a concentration of 6 molar. A control reaction contained obesity protein analog precursor (SEQ ID NO:17) in which the intramolecular disulfide bond was intact. The concentration of obesity protein analog (SEQ ID NO:6) was determined by reverse-phase HPLC. Obesity protein analog was produced at about the same extent whether mixed disulfide precursor or precursor having an intact intramolecular disulfide bond was used in the reation, as seen in Table 2.

TABLE 2 dDAP-Catalyzed Conversion: Mixed Disulfide Precursor vs. Precursor with Intramolecular Disulfide Bond

| | % of Precursor Converted to Obesity Protein Analog | |
|---|---|---|
| Time (min) | Precursor with Intramolecular Disulfide Bond | Mixed Disulfide Precursor |
| 2 | 32 | 25 |
| 5 | 51 | 50 |
| 10 | 75 | 72 |
| 15 | 90 | 84 |
| 20 | 96 | 80 |

EXAMPLE 5

Effect of Precursor Concentration

At a ratio of 0.5 U dDAP activity added per gram of precursor (U/gram), conversion to obesity protein analog (SEQ ID NO:6) reached 100% within 2 hours when the concentration of obesity protein analog precursor (SEQ ID NO:17) was 25 mg/mL, while it took between 3 and 7 hours to reach 100% conversion when the precursor concentration was only 2.3 mg/mL. These comparative reactions were carried out in 6 molar urea, pH 5, at 23°–24° C.

EXAMPLE 6

Effect of dDAP to Precursor Ratio

Using an analog precursor of SEQ ID NO:17 at a concentration of 25 mg/mL, in 6 molar urea, pH 5, 23° C., the following times were required to reach at least 90% conversion: 0.5 U/mg, within 2 hours; 0.25 u/mg, within 4 hours; 0.125 U/mg, within 20 hours; and 0.075 U/mg, within 27 hours.

EXAMPLE 7

Preparation and Use of Immobilized dDAP

A resin (Q Sepharose®, Pharmacia) was prepared in 50 mM acetic acid, pH 3.2 by first settling it in a graduated test tube to measure the volume. dDAP was added to give a concentration of 5 U per mL of settled resin, and allowed to mix for at least 30 minutes. The resin was packed in a column (0.5 cm×4 cm), and was equilibrated in 50 mM acetic acid, pH 3.2, at 24° C. Obesity protein analog precursor (SEQ ID NO:17, 2.7 mg/mL) in 6 molar urea, pH 5, and at the same temperature was passed through the packed bed at various flow rates. The concentration of obesity protein analog (SEQ ID NO:6) in the eluate was determined by reverse-phase HPLC. With a residence time (packed bed volume divided by flow rate) of 1 minute, 97% conversion to obesity protein analog was found under the described conditions.

---

We claim:

1. A process for preparing an obesity protein analog, which comprises contacting an obesity protein analog precursor with dDAP.

2. The process of claim 1, wherein the obesity protein analog precursor is contacted with dDAP in a solution having pH between about 2.4 and about 4.5.

3. The process of claim 2, wherein the obesity protein analog precursor is comprised of a dipeptide attached to the amino-terminus of an obesity protein analog.

4. The process of claim 3, wherein the dipeptide attached to the amino-terminus is selected from the group consisting of Met-Arg, Met-Asp, and Met-Tyr.

5. The process of claim 4, wherein the dipeptide attached to the amino-terminus is Met-Arg.

6. The process of claim 5, wherein the obesity protein analog produced is selected from the group consisting of the proteins represented by SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

7. The process of claim 1, which further comprises contacting in the presence of urea.

8. The process of claim 7, wherein the urea concentration is between about 4 molar and about 7 molar.

9. The process of claim 8, wherein the obesity protein analog precursor is contacted with dDAP in a solution having pH between about pH 4 and about pH 7.

10. The process of claim 9, wherein the obesity protein analog precursor is comprised of a dipeptide attached to the amino-terminus of the obesity protein analog.

11. The process of claim 10, wherein the dipeptide attached to the amino-terminus is selected from the group consisting of Met-Arg, Met-Asp, and Met-Tyr.

12. The process of claim 11, wherein the dipeptide attached to the amino-terminus is Met-Arg.

13. The process of claim 12, wherein the obesity protein analog produced is selected from the group consisting of the proteins represented by SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

14. The process of claim 1, wherein dDAP is immobilized on a suitable support surface.

15. The process of claim 7, wherein dDAP is immobilized on a suitable support surface.

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
    ( A ) NAME/KEY: Modified-site
    ( B ) LOCATION: 4
    ( D ) OTHER INFORMATION: /product="none"
        / label= Xaa
        / note= "Xaa at position 4 is Gln or Glu;"

( i x ) FEATURE:
    ( A ) NAME/KEY: Modified-site
    ( B ) LOCATION: 7
    ( D ) OTHER INFORMATION: /product="OTHER"
        / label= Xaa
        / note= "Xaa at position 7 is Gln or Glu"

( i x ) FEATURE:
    ( A ) NAME/KEY: Modified-site
    ( B ) LOCATION: 22
    ( D ) OTHER INFORMATION: /product="OTHER"
        / label= Xaa
        / note= "Xaa at position 22 is Gln, Asn, or Asp"

( i x ) FEATURE:
    ( A ) NAME/KEY: Modified-site
    ( B ) LOCATION: 27
    ( D ) OTHER INFORMATION: /product="OTHER"
        / label= Xaa
        / note= "Xaa at position 27 is Thr or Ala"

( i x ) FEATURE:
    ( A ) NAME/KEY: Modified-site
    ( B ) LOCATION: 28
    ( D ) OTHER INFORMATION: /product="OTHER"
        / label= Xaa
        / note= "Xaa at position 28 is Gln, Glu, or absent"

( i x ) FEATURE:
    ( A ) NAME/KEY: Modified-site
    ( B ) LOCATION: 34
    ( D ) OTHER INFORMATION: /product="OTHER"
        / label= Xaa
        / note= "Xaa at position 34 is Gln or Glu"

( i x ) FEATURE:
    ( A ) NAME/KEY: Modified-site
    ( B ) LOCATION: 54
    ( D ) OTHER INFORMATION: /product="OTHER"
        / label= Xaa
        / note= "Xaa at position 54 is Met, methionine sulfoxide,
        Leu, Ile, Val, Ala, or Gly"

( i x ) FEATURE:
    ( A ) NAME/KEY: Modified-site
    ( B ) LOCATION: 56
    ( D ) OTHER INFORMATION: /product="OTHER"
        / label= Xaa
        / note= "Xaa at position 56 is Gln or Glu"

( i x ) FEATURE:
    ( A ) NAME/KEY: Modified-site
    ( B ) LOCATION: 62
    ( D ) OTHER INFORMATION: /product="OTHER"
        / label= Xaa
        / note= "Xaa at position 62 is Gln or Glu"

( i x ) FEATURE:
    ( A ) NAME/KEY: Modified-site
    ( B ) LOCATION: 63
    ( D ) OTHER INFORMATION: /product="OTHER"
        / label= Xaa
        / note= "Xaa at position 63 is Gln or Glu"

( i x ) FEATURE:

```
            ( A ) NAME/KEY: Modified-site
            ( B ) LOCATION: 68
            ( D ) OTHER INFORMATION: /product="OTHER"
                    / label= Xaa
                    / note= "Xaa at position 68 is Met, methionine sulfoxide,
                    Leu, Ile, Val, Ala, or Gly"

( i x ) FEATURE:
            ( A ) NAME/KEY: Modified-site
            ( B ) LOCATION: 72
            ( D ) OTHER INFORMATION: /product="OTHER"
                    / label= Xaa
                    / note= "Xaa at position 72 is Gln, Asn, or Asp"

( i x ) FEATURE:
            ( A ) NAME/KEY: Modified-site
            ( B ) LOCATION: 75
            ( D ) OTHER INFORMATION: /product="OTHER"
                    / label= Xaa
                    / note= "Xaa at position 75 is Gln or Glu"

( i x ) FEATURE:
            ( A ) NAME/KEY: Modified-site
            ( B ) LOCATION: 78
            ( D ) OTHER INFORMATION: /product="OTHER"
                    / label= Xaa
                    / note= "Xaa at position 78 is Gln, Asn, or Asp"

( i x ) FEATURE:
            ( A ) NAME/KEY: Modified-site
            ( B ) LOCATION: 82
            ( D ) OTHER INFORMATION: /product="OTHER"
                    / label= Xaa
                    / note= "Xaa at position 82 is Gln, Asn, or Asp"

( i x ) FEATURE:
            ( A ) NAME/KEY: Modified-site
            ( B ) LOCATION: 100
            ( D ) OTHER INFORMATION: /product="OTHER"
                    / label= Xaa
                    / note= "Xaa at position 100 is Gln, Trp, Tyr, Phe, Ile,
                    Val, or Leu"

( i x ) FEATURE:
            ( A ) NAME/KEY: Modified-site
            ( B ) LOCATION: 108
            ( D ) OTHER INFORMATION: /product="OTHER"
                    / label= Xaa
                    / note= "Xaa at position 108 is Asp or Glu"

( i x ) FEATURE:
            ( A ) NAME/KEY: Modified-site
            ( B ) LOCATION: 130
            ( D ) OTHER INFORMATION: /product="OTHER"
                    / label= Xaa
                    / note= "Xaa at position 130 is Gln or Glu"

( i x ) FEATURE:
            ( A ) NAME/KEY: Modified-site
            ( B ) LOCATION: 134
            ( D ) OTHER INFORMATION: /product="OTHER"
                    / label= Xaa
                    / note= "Xaa at position 134 is Gln or Glu"

( i x ) FEATURE:
            ( A ) NAME/KEY: Modified-site
            ( B ) LOCATION: 136
            ( D ) OTHER INFORMATION: /product="OTHER"
                    / label= Xaa
                    / note= "Xaa at position 136 is Met, methionine sulfoxide,
                    Leu, Ile, Val, Ala, or Gly"

( i x ) FEATURE:
            ( A ) NAME/KEY: Modified-site
            ( B ) LOCATION: 138
            ( D ) OTHER INFORMATION: /product="OTHER"
                    / label= Xaa
                    / note= "Xaa at position 138 is Gln, Trp, Tyr, Phe, Ile,
                    Val, or Leu"
```

( i x ) FEATURE:
       ( A ) NAME/KEY: Modified-site
       ( B ) LOCATION: 139
       ( D ) OTHER INFORMATION: /product="OTHER"
            / label= Xaa
            / note= "Xaa at position 139 is Gln or Glu"

( x i ) SEQUENCE DESCRIPTION: SEQ ID NO:1:

```
Val  Pro  Ile  Xaa  Lys  Val  Xaa  Asp  Asp  Thr  Lys  Thr  Leu  Ile  Lys  Thr
 1              5                        10                       15
Ile  Val  Thr  Arg  Ile  Xaa  Asp  Ile  Ser  His  Xaa  Xaa  Ser  Val  Ser  Ser
               20                   25                            30
Lys  Xaa  Lys  Val  Thr  Gly  Leu  Asp  Phe  Ile  Pro  Gly  Leu  His  Pro  Ile
          35                        40                  45
Leu  Thr  Leu  Ser  Lys  Xaa  Asp  Xaa  Thr  Leu  Ala  Val  Tyr  Xaa  Xaa  Ile
 50                            55                       60
Leu  Thr  Ser  Xaa  Pro  Ser  Arg  Xaa  Val  Ile  Xaa  Ile  Ser  Xaa  Asp  Leu
 65                       70                       75                       80
Glu  Xaa  Leu  Arg  Asp  Leu  Leu  His  Val  Leu  Ala  Phe  Ser  Lys  Ser  Cys
                    85                  90                            95
His  Leu  Pro  Xaa  Ala  Ser  Gly  Leu  Glu  Thr  Leu  Xaa  Ser  Leu  Gly  Gly
               100                      105                      110
Val  Leu  Glu  Ala  Ser  Gly  Tyr  Ser  Thr  Glu  Val  Val  Ala  Leu  Ser  Arg
          115                      120                      125
Leu  Xaa  Gly  Ser  Leu  Xaa  Asp  Xaa  Leu  Xaa  Xaa  Leu  Asp  Leu  Ser  Pro
     130                      135                      140
Gly  Cys
145
```

( 2 ) INFORMATION FOR SEQ ID NO:2:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( i x ) FEATURE:
        ( A ) NAME/KEY: Modified-site
        ( B ) LOCATION: 2
        ( D ) OTHER INFORMATION: /product="OTHER"
             / label= Xaa
             / note= "Xaa at position 2 is any amino acid except Pro"

( i x ) FEATURE:
        ( A ) NAME/KEY: Modified-site
        ( B ) LOCATION: 6
        ( D ) OTHER INFORMATION: /product="OTHER"
             / label= Xaa
             / note= "Xaa at position 6 is Gln or Glu"

( i x ) FEATURE:
        ( A ) NAME/KEY: Modified-site
        ( B ) LOCATION: 9
        ( D ) OTHER INFORMATION: /product="OTHER"
             / label= Xaa
             / note= "Xaa at position 9 is Gln or Glu"

( i x ) FEATURE:
        ( A ) NAME/KEY: Modified-site
        ( B ) LOCATION: 24

```
            ( D ) OTHER INFORMATION: /product="OTHER"
                    / label= Xaa
                    / note= "Xaa at position 24 is Gln, Asn, or Asp"

( i x ) FEATURE:
            ( A ) NAME/KEY: Modified-site
            ( B ) LOCATION: 29
            ( D ) OTHER INFORMATION: /product="OTHER"
                    / label= Xaa
                    / note= "Xaa at position 29 is Thr or Ala"

( i x ) FEATURE:
            ( A ) NAME/KEY: Modified-site
            ( B ) LOCATION: 30
            ( D ) OTHER INFORMATION: /product="OTHER"
                    / label= Xaa
                    / note= "Xaa at position 30 is Gln, Glu, or absent"

( i x ) FEATURE:
            ( A ) NAME/KEY: Modified-site
            ( B ) LOCATION: 36
            ( D ) OTHER INFORMATION: /product="OTHER"
                    / label= Xaa
                    / note= "Xaa at position 36 is Gln or Glu"

( i x ) FEATURE:
            ( A ) NAME/KEY: Modified-site
            ( B ) LOCATION: 56
            ( D ) OTHER INFORMATION: /product="OTHER"
                    / label= Xaa
                    / note= "Xaa at position 56 is Met, methionine sulfoxide,
                    Leu, Ile, Val, Ala, or Gly"

( i x ) FEATURE:
            ( A ) NAME/KEY: Modified-site
            ( B ) LOCATION: 58
            ( D ) OTHER INFORMATION: /product="OTHER"
                    / label= Xaa
                    / note= "Xaa at position 58 is Gln or Glu"

( i x ) FEATURE:
            ( A ) NAME/KEY: Modified-site
            ( B ) LOCATION: 64
            ( D ) OTHER INFORMATION: /product="OTHER"
                    / label= Xaa
                    / note= "Xaa at position 64 is Gln or Glu"

( i x ) FEATURE:
            ( A ) NAME/KEY: Modified-site
            ( B ) LOCATION: 65
            ( D ) OTHER INFORMATION: /product="OTHER"
                    / label= Xaa
                    / note= "Xaa at position 65 is Gln or Glu"

( i x ) FEATURE:
            ( A ) NAME/KEY: Modified-site
            ( B ) LOCATION: 70
            ( D ) OTHER INFORMATION: /product="OTHER"
                    / label= Xaa
                    / note= "Xaa at position 70 is Met, methionine sulfoxide,
                    Leu, Ile, Val, Ala, or Gly"

( i x ) FEATURE:
            ( A ) NAME/KEY: Modified-site
            ( B ) LOCATION: 74
            ( D ) OTHER INFORMATION: /product="OTHER"
                    / label= Xaa
                    / note= "Xaa at position 74 is Gln, Asn, or Asp"

( i x ) FEATURE:
            ( A ) NAME/KEY: Modified-site
            ( B ) LOCATION: 77
            ( D ) OTHER INFORMATION: /product="OTHER"
                    / label= Xaa
                    / note= "Xaa at position 77 is Gln or Glu"

( i x ) FEATURE:
            ( A ) NAME/KEY: Modified-site
            ( B ) LOCATION: 80
            ( D ) OTHER INFORMATION: /product="OTHER"
```

/ label= Xaa
/ note= "Xaa at position 80 is Gln, Asn, or Asp"

( i x ) FEATURE:
 ( A ) NAME/KEY: Modified-site
 ( B ) LOCATION: 84
 ( D ) OTHER INFORMATION: /product="OTHER"
  / label= Xaa
  / note= "Xaa at position 84 is Gln, Asn, or Asp"

( i x ) FEATURE:
 ( A ) NAME/KEY: Modified-site
 ( B ) LOCATION: 102
 ( D ) OTHER INFORMATION: /product="OTHER"
  / label= Xaa
  / note= "Xaa at position 102 is Gln, Trp, Tyr, Phe, Ile, Val, or Leu"

( i x ) FEATURE:
 ( A ) NAME/KEY: Modified-site
 ( B ) LOCATION: 110
 ( D ) OTHER INFORMATION: /product="OTHER"
  / label= Xaa
  / note= "Xaa at position 110 is Asp or Glu"

( i x ) FEATURE:
 ( A ) NAME/KEY: Modified-site
 ( B ) LOCATION: 132
 ( D ) OTHER INFORMATION: /product="OTHER"
  / label= Xaa
  / note= "Xaa at position 132 is Gln or Glu"

( i x ) FEATURE:
 ( A ) NAME/KEY: Modified-site
 ( B ) LOCATION: 136
 ( D ) OTHER INFORMATION: /product="OTHER"
  / label= Xaa
  / note= "Xaa at position 136 is Gln or Glu"

( i x ) FEATURE:
 ( A ) NAME/KEY: Modified-site
 ( B ) LOCATION: 138
 ( D ) OTHER INFORMATION: /product="OTHER"
  / label= Xaa
  / note= "Xaa at position 138 is Met, methionine sulfoxide, Leu, Ile, Val, Ala, or Gly"

( i x ) FEATURE:
 ( A ) NAME/KEY: Modified-site
 ( B ) LOCATION: 140
 ( D ) OTHER INFORMATION: /product="OTHER"
  / label= Xaa
  / note= "Xaa at position 140 is Gln, Trp, Tyr, Phe, Ile, Val, or Leu"

( i x ) FEATURE:
 ( A ) NAME/KEY: Modified-site
 ( B ) LOCATION: 141
 ( D ) OTHER INFORMATION: /product="OTHER"
  / label= Xaa
  / note= "Xaa at position 141 is Gln or Glu"

( x i ) SEQUENCE DESCRIPTION: SEQ ID NO:2:

```
Met  Xaa  Val  Pro  Ile  Xaa  Lys  Val  Xaa  Asp  Asp  Thr  Lys  Thr  Leu  Ile
 1                   5                        10                        15

Lys  Thr  Ile  Val  Thr  Arg  Ile  Xaa  Asp  Ile  Ser  His  Xaa  Xaa  Ser  Val
               20                   25                        30

Ser  Ser  Lys  Xaa  Lys  Val  Thr  Gly  Leu  Asp  Phe  Ile  Pro  Gly  Leu  His
          35                        40                   45

Pro  Ile  Leu  Thr  Leu  Ser  Lys  Xaa  Asp  Xaa  Thr  Leu  Ala  Val  Tyr  Xaa
     50                        55                        60

Xaa  Ile  Leu  Thr  Ser  Xaa  Pro  Ser  Arg  Xaa  Val  Ile  Xaa  Ile  Ser  Xaa
65                        70                        75                        80

Asp  Leu  Glu  Xaa  Leu  Arg  Asp  Leu  Leu  His  Val  Leu  Ala  Phe  Ser  Lys
```

|   |   |   |   |   | 85 |   |   |   |   | 90 |   |   |   |   | 95 |   |   |
|---|---|---|---|---|---|---|---|---|---|---|---|---|---|---|---|---|---|

Ser Cys His Leu Pro Xaa Ala Ser Gly Leu Glu Thr Leu Xaa Ser Leu
                100                     105                   110

Gly Gly Val Leu Glu Ala Ser Gly Tyr Ser Thr Glu Val Val Ala Leu
            115                 120                 125

Ser Arg Leu Xaa Gly Ser Leu Xaa Asp Xaa Leu Xaa Xaa Leu Asp Leu
        130             135             140

Ser Pro Gly Cys
145

( 2 ) INFORMATION FOR SEQ ID NO:3:

( i ) SEQUENCE CHARACTERISTICS:
      ( A ) LENGTH: 146 amino acids
      ( B ) TYPE: amino acid
      ( C ) STRANDEDNESS: single
      ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
      ( A ) NAME/KEY: Modified-site
      ( B ) LOCATION: 77
      ( D ) OTHER INFORMATION: /note= "Ser at position 77 is
          replaced with Ala"

( i x ) FEATURE:
      ( A ) NAME/KEY: Modified-site
      ( B ) LOCATION: 97
      ( D ) OTHER INFORMATION: /note= "His at position 97 is
          replaced with Gln, Asn, Ala, Gly, Ser, or Pro"

( i x ) FEATURE:
      ( A ) NAME/KEY: Modified-site
      ( B ) LOCATION: 100
      ( D ) OTHER INFORMATION: /note= "Trp at position 100 is
          replaced with Ala, Glu, Asp, Asn, Met, Ser, Thr, or Gly"

( i x ) FEATURE:
      ( A ) NAME/KEY: Modified-site
      ( B ) LOCATION: 101
      ( D ) OTHER INFORMATION: /note= "Ala at position 101 is
          replaced with Ser, Asn, Gly, His, Pro, Thr, or Val"

( i x ) FEATURE:
      ( A ) NAME/KEY: Modified-site
      ( B ) LOCATION: 102
      ( D ) OTHER INFORMATION: /note= "Ser at position 102 is
          replaced with Arg"

( i x ) FEATURE:
      ( A ) NAME/KEY: Modified-site
      ( B ) LOCATION: 103
      ( D ) OTHER INFORMATION: /note= "Gly at position 103 is
          replaced with Ala"

( i x ) FEATURE:
      ( A ) NAME/KEY: Modified-site
      ( B ) LOCATION: 105
      ( D ) OTHER INFORMATION: /note= "Glu at position 105 is
          replaced with Gln"

( i x ) FEATURE:
      ( A ) NAME/KEY: Modified-site
      ( B ) LOCATION: 106
      ( D ) OTHER INFORMATION: /note= "Thr at position 106 is
          replaced with Lys or Ser"

( i x ) FEATURE:

(A) NAME/KEY: Modified-site
(B) LOCATION: 107
(D) OTHER INFORMATION: /note= "Leu at position 107 is
replaced with Pro"

(ix) FEATURE:
(A) NAME/KEY: Modified-site
(B) LOCATION: 111
(D) OTHER INFORMATION: /note= "Gly at position 111 is
replaced with Asp"

(ix) FEATURE:
(A) NAME/KEY: Modified-site
(B) LOCATION: 118
(D) OTHER INFORMATION: /note= "Gly at position 118 is
repaced with Leu"

(ix) FEATURE:
(A) NAME/KEY: Modified-site
(B) LOCATION: 138
(D) OTHER INFORMATION: /note= "Trp at position 138 is
replaced with Ala, Glu, Asp, Asn, Met, Ser, Thr, or Gly"

(xi) SEQUENCE DESCRIPTION: SEQ ID NO:3:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |

| Ile | Val | Thr | Arg | Ile | Asn | Asp | Ile | Ser | His | Thr | Gln | Ser | Val | Ser | Ser |
|---|---|---|---|---|---|---|---|---|---|---|---|---|---|---|---|
| | | | 20 | | | | | 25 | | | | | 30 | | |

| Lys | Gln | Lys | Val | Thr | Gly | Leu | Asp | Phe | Ile | Pro | Gly | Leu | His | Pro | Ile |
|---|---|---|---|---|---|---|---|---|---|---|---|---|---|---|---|
| | | 35 | | | | | 40 | | | | | 45 | | | |

| Leu | Thr | Leu | Ser | Lys | Met | Asp | Gln | Thr | Leu | Ala | Val | Tyr | Gln | Gln | Ile |
|---|---|---|---|---|---|---|---|---|---|---|---|---|---|---|---|
| | 50 | | | | | 55 | | | | | 60 | | | | |

| Leu | Thr | Ser | Met | Pro | Ser | Arg | Asn | Val | Ile | Gln | Ile | Ser | Asn | Asp | Leu |
|---|---|---|---|---|---|---|---|---|---|---|---|---|---|---|---|
| 65 | | | | | 70 | | | | | 75 | | | | | 80 |

| Glu | Asn | Leu | Arg | Asp | Leu | Leu | His | Val | Leu | Ala | Phe | Ser | Lys | Ser | Cys |
|---|---|---|---|---|---|---|---|---|---|---|---|---|---|---|---|
| | | | | 85 | | | | | 90 | | | | | 95 | |

| His | Leu | Pro | Trp | Ala | Ser | Gly | Leu | Glu | Thr | Leu | Asp | Ser | Leu | Gly | Gly |
|---|---|---|---|---|---|---|---|---|---|---|---|---|---|---|---|
| | | | 100 | | | | | 105 | | | | | 110 | | |

| Val | Leu | Glu | Ala | Ser | Gly | Tyr | Ser | Thr | Glu | Val | Val | Ala | Leu | Ser | Arg |
|---|---|---|---|---|---|---|---|---|---|---|---|---|---|---|---|
| | | 115 | | | | | 120 | | | | | 125 | | | |

| Leu | Gln | Gly | Ser | Leu | Gln | Asp | Met | Leu | Trp | Gln | Leu | Asp | Leu | Ser | Pro |
|---|---|---|---|---|---|---|---|---|---|---|---|---|---|---|---|
| | 130 | | | | | 135 | | | | | 140 | | | | |

| Gly | Cys |
|---|---|
| 145 | |

(2) INFORMATION FOR SEQ ID NO:4:

(i) SEQUENCE CHARACTERISTICS:
(A) LENGTH: 146 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (ix) FEATURE:
(A) NAME/KEY: Modified-site
(B) LOCATION: 1
(D) OTHER INFORMATION: /product="OTHER"
/ label= Xaa
/ note= "Xaa at position 1 is Val or absent"

(ix) FEATURE:

( A ) NAME/KEY: Modified-site
              ( B ) LOCATION: 2
              ( D ) OTHER INFORMATION: /product="OTHER"
                      / label= Xaa
                      / note= "Xaa at position 2 is Pro or absent"

( i x ) FEATURE:
              ( A ) NAME/KEY: Modified-site
              ( B ) LOCATION: 22
              ( D ) OTHER INFORMATION: /product="OTHER"
                      / label= Xaa
                      / note= "Xaa at position 22 is Asn or Ser"

( i x ) FEATURE:
              ( A ) NAME/KEY: Modified-site
              ( B ) LOCATION: 28
              ( D ) OTHER INFORMATION: /product="OTHER"
                      / label= Xaa
                      / note= "Xaa at position 28 is Gln or absent"

( i x ) FEATURE:
              ( A ) NAME/KEY: Modified-site
              ( B ) LOCATION: 72
              ( D ) OTHER INFORMATION: /product="OTHER"
                      / label= Xaa
                      / note= "Xaa at position 72 is Asn, Gln, Glu, or Asp"

( i x ) FEATURE:
              ( A ) NAME/KEY: Modified-site
              ( B ) LOCATION: 73
              ( D ) OTHER INFORMATION: /product="OTHER"
                      / label= Xaa
                      / note= "Xaa at position 73 is Val or Met"

( i x ) FEATURE:
              ( A ) NAME/KEY: Modified-site
              ( B ) LOCATION: 100
              ( D ) OTHER INFORMATION: /product="OTHER"
                      / label= Xaa
                      / note= "Xaa at position 100 is Trp, Gln, Glu, Asp, Ser,
                        Thr, Lys, His, or Arg"

( i x ) FEATURE:
              ( A ) NAME/KEY: Modified-site
              ( B ) LOCATION: 138
              ( D ) OTHER INFORMATION: /product="OTHER"
                      / label= Xaa
                      / note= "Xaa at position 138 is Trp, Gln, Glu, Asp, Ser,
                        Thr, Lys, His, or Arg"

( i x ) FEATURE:
              ( A ) NAME/KEY: Modified-site
              ( B ) LOCATION: 1
              ( D ) OTHER INFORMATION: /product="OTHER"
                      / label= Xaa
                      / note= "Xaa at position 1 is replaced with Glu, Asp, Ser,
                        Thr, Lys, His, or Arg"

( i x ) FEATURE:
              ( A ) NAME/KEY: Modified-site
              ( B ) LOCATION: 2
              ( D ) OTHER INFORMATION: /product="OTHER"
                      / label= Xaa
                      / note= "Xaa at position 2 is replaced with Glu, Asp, Ser,
                        Thr, Lys, His, or Arg"

( i x ) FEATURE:
              ( A ) NAME/KEY: Modified-site
              ( B ) LOCATION: 3
              ( D ) OTHER INFORMATION: /note= "Ile at position 3 is
                        replaced with Glu, Asp, Arg, Lys, or His"

( i x ) FEATURE:
              ( A ) NAME/KEY: Modified-site
              ( B ) LOCATION: 30
              ( D ) OTHER INFORMATION: /note= "Val at position 30 is
                        replaced with Glu, Asp, Arg, Lys, or His"

( i x ) FEATURE:
              ( A ) NAME/KEY: Modified-site (B) LOCATION: 36
(D) OTHER INFORMATION: /note= "Val at position 36 is
replaced with Glu, Asp, Arg, Lys, or His"

(ix) FEATURE:
(A) NAME/KEY: Modified-site
(B) LOCATION: 41
(D) OTHER INFORMATION: /note= "Phe at position 41 is
replaced with Glu, Asp, Arg, Lys, or His"

(ix) FEATURE:
(A) NAME/KEY: Modified-site
(B) LOCATION: 42
(D) OTHER INFORMATION: /note= "Ile at position 42 is
replaced with Glu, Asp, Arg, Lys, or His"

(ix) FEATURE:
(A) NAME/KEY: Modified-site
(B) LOCATION: 43
(D) OTHER INFORMATION: /note= "Pro at position 43 is
repaced with Glu, Asp, Arg, Lys, or His"

(ix) FEATURE:
(A) NAME/KEY: Modified-site
(B) LOCATION: 45
(D) OTHER INFORMATION: /note= "Leu at position 45 is
replaced with Glu, Asp, Arg, Lys, or His"

(ix) FEATURE:
(A) NAME/KEY: Modified-site
(B) LOCATION: 46
(D) OTHER INFORMATION: /note= "His at position 46 is
replaced with Glu, Asp, Arg, or Lys"

(ix) FEATURE:
(A) NAME/KEY: Modified-site
(B) LOCATION: 47
(D) OTHER INFORMATION: /note= "Pro at position 47 is
replaced with Glu, Asp, Arg, Lys, or His"

(ix) FEATURE:
(A) NAME/KEY: Modified-site
(B) LOCATION: 48
(D) OTHER INFORMATION: /note= "Ile at position 48 is
replaced with Glu, Asp, Arg, Lys, or His"

(ix) FEATURE:
(A) NAME/KEY: Modified-site
(B) LOCATION: 49
(D) OTHER INFORMATION: /note= "Leu at position 49 is
replaced with Glu, Asp, Arg, Lys, or His"

(ix) FEATURE:
(A) NAME/KEY: Modified-site
(B) LOCATION: 50
(D) OTHER INFORMATION: /note= "Thr at position 50 is
replaced with Glu, Asp, Arg, Lys, or His"

(ix) FEATURE:
(A) NAME/KEY: Modified-site
(B) LOCATION: 74
(D) OTHER INFORMATION: /note= "Ile at position 74 is
repaced with Gln, Glu, Asp, Arg, Lys, His, Thr, or Ser"

(ix) FEATURE:
(A) NAME/KEY: Modified-site
(B) LOCATION: 89
(D) OTHER INFORMATION: /note= "Val at position 89 is
replaced with Gln, Glu, Asp, Arg, Lys, His, Thr, or Ser"

(ix) FEATURE:
(A) NAME/KEY: Modified-site
(B) LOCATION: 92
(D) OTHER INFORMATION: /note= "Phe at position 92 is
replaced with Gln, Glu, Asp, Arg, Lys, His, Thr, or Ser"

(ix) FEATURE:
(A) NAME/KEY: Modified-site
(B) LOCATION: 99
(D) OTHER INFORMATION: /note= "Pro at position 99 is -continued replaced with Gln, Glu, Asp, Arg, Lys, His, Thr, or Ser"

(ix) FEATURE:
    (A) NAME/KEY: Modified-site
    (B) LOCATION: 142
    (D) OTHER INFORMATION: /note= "Leu at position 142 is
        replaced with Glu, Asp, Arg, Lys, or His"

(xi) SEQUENCE DESCRIPTION: SEQ ID NO:4:

```
Xaa Xaa Ile Gln Lys Val Gln Asp Asp Thr Lys Thr Leu Ile Lys Thr
1               5                   10                  15
Ile Val Thr Arg Ile Xaa Asp Ile Ser His Thr Xaa Ser Val Ser Ser
                20          25              30
Lys Gln Lys Val Thr Gly Leu Asp Phe Ile Pro Gly Leu His Pro Ile
            35              40              45
Leu Thr Leu Ser Lys Met Asp Gln Thr Leu Ala Val Tyr Gln Gln Ile
    50              55                      60
Leu Thr Ser Met Pro Ser Arg Xaa Xaa Ile Gln Ile Ser Asn Asp Leu
65                  70              75                      80
Glu Asn Leu Arg Asp Leu Leu His Val Leu Ala Phe Ser Lys Ser Cys
                85              90                  95
His Leu Pro Xaa Ala Ser Gly Leu Glu Thr Leu Asp Ser Leu Gly Gly
            100             105                     110
Val Leu Glu Ala Ser Gly Tyr Ser Thr Glu Val Val Ala Leu Ser Arg
            115             120                 125
Leu Gln Gly Ser Leu Gln Asp Met Leu Xaa Gln Leu Asp Leu Ser Pro
    130                 135             140
Gly Cys
145
```

(2) INFORMATION FOR SEQ ID NO:5:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (ix) FEATURE:
        (A) NAME/KEY: Modified-site
        (B) LOCATION: 22
        (D) OTHER INFORMATION: /product="OTHER"
            / label= Xaa
            / note= "Xaa at position 22 is Asn or Ser"

(ix) FEATURE:
        (A) NAME/KEY: Modified-site
        (B) LOCATION: 28
        (D) OTHER INFORMATION: /product="OTHER"
            / label= Xaa
            / note= "Xaa at position 28 is Gln or absent"

(ix) FEATURE:
        (A) NAME/KEY: Modified-site
        (B) LOCATION: 72
        (D) OTHER INFORMATION: /product="OTHER"
            / label= Xaa
            / note= "Xaa at position 72 is Asn, Gln, Glu, or Asp"

(ix) FEATURE:
        (A) NAME/KEY: Modified-site (B) LOCATION: 73
(D) OTHER INFORMATION: /product="OTHER"
  / label= Xaa
  / note= "Xaa at position 73 is Val or Met"

(ix) FEATURE:
  (A) NAME/KEY: Modified-site
  (B) LOCATION: 100
  (D) OTHER INFORMATION: /note= "Trp at position 100 is replaced with Glu, Asp, His, Lys, or Arg"

(ix) FEATURE:
  (A) NAME/KEY: Modified-site
  (B) LOCATION: 138
  (D) OTHER INFORMATION: /note= "Trp at position 138 is replaced with Glu, Asp, His, Lys, or Arg"

(xi) SEQUENCE DESCRIPTION: SEQ ID NO:5:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |

| Ile | Val | Thr | Arg | Ile | Asn | Asp | Ile | Ser | His | Thr | Xaa | Ser | Val | Ser | Ser |
|---|---|---|---|---|---|---|---|---|---|---|---|---|---|---|---|
| | | | 20 | | | | | 25 | | | | | 30 | | |

| Lys | Gln | Lys | Val | Thr | Gly | Leu | Asp | Phe | Ile | Pro | Gly | Leu | His | Pro | Ile |
|---|---|---|---|---|---|---|---|---|---|---|---|---|---|---|---|
| | | 35 | | | | | 40 | | | | | 45 | | | |

| Leu | Thr | Leu | Ser | Lys | Met | Asp | Gln | Thr | Leu | Ala | Val | Tyr | Gln | Gln | Ile |
|---|---|---|---|---|---|---|---|---|---|---|---|---|---|---|---|
| | 50 | | | | | 55 | | | | | 60 | | | | |

| Leu | Thr | Ser | Met | Pro | Ser | Arg | Asn | Val | Ile | Gln | Ile | Ser | Asn | Asp | Leu |
|---|---|---|---|---|---|---|---|---|---|---|---|---|---|---|---|
| 65 | | | | | 70 | | | | | 75 | | | | | 80 |

| Glu | Asn | Leu | Arg | Asp | Leu | Leu | His | Val | Leu | Ala | Phe | Ser | Lys | Ser | Cys |
|---|---|---|---|---|---|---|---|---|---|---|---|---|---|---|---|
| | | | | 85 | | | | | 90 | | | | | 95 | |

| His | Leu | Pro | Trp | Ala | Ser | Gly | Leu | Glu | Thr | Leu | Asp | Ser | Leu | Gly | Gly |
|---|---|---|---|---|---|---|---|---|---|---|---|---|---|---|---|
| | | | 100 | | | | | 105 | | | | | 110 | | |

| Val | Leu | Glu | Ala | Ser | Gly | Tyr | Ser | Thr | Glu | Val | Val | Ala | Leu | Ser | Arg |
|---|---|---|---|---|---|---|---|---|---|---|---|---|---|---|---|
| | | | 115 | | | | | 120 | | | | | 125 | | |

| Leu | Gln | Gly | Ser | Leu | Gln | Asp | Met | Leu | Trp | Gln | Leu | Asp | Leu | Ser | Pro |
|---|---|---|---|---|---|---|---|---|---|---|---|---|---|---|---|
| | 130 | | | | | 135 | | | | | 140 | | | | |

| Gly | Cys |
|---|---|
| 145 | |

(2) INFORMATION FOR SEQ ID NO:6:

(i) SEQUENCE CHARACTERISTICS:
    (A) LENGTH: 146 amino acids
    (B) TYPE: amino acid
    (C) STRANDEDNESS: single
    (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:6:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |

| Ile | Val | Thr | Arg | Ile | Asn | Asp | Ile | Ser | His | Thr | Gln | Ser | Val | Ser | Ser |
|---|---|---|---|---|---|---|---|---|---|---|---|---|---|---|---|
| | | | 20 | | | | | 25 | | | | | 30 | | |

| Lys | Gln | Lys | Val | Thr | Gly | Leu | Asp | Phe | Ile | Pro | Gly | Leu | His | Pro | Ile |
|---|---|---|---|---|---|---|---|---|---|---|---|---|---|---|---|
| | | 35 | | | | | 40 | | | | | 45 | | | |

| Leu | Thr | Leu | Ser | Lys | Met | Asp | Gln | Thr | Leu | Ala | Val | Tyr | Gln | Gln | Ile |
|---|---|---|---|---|---|---|---|---|---|---|---|---|---|---|---|
| | 50 | | | | | 55 | | | | | 60 | | | | |

| | | | | | | | | | | | | | | | |
|---|---|---|---|---|---|---|---|---|---|---|---|---|---|---|---|
|Leu|Thr|Ser|Met|Pro|Ser|Arg|Asn|Val|Ile|Gln|Ile|Ser|Asn|Asp|Leu|
|65| | | |70| | | | |75| | | | | |80|
|Glu|Asn|Leu|Arg|Asp|Leu|Leu|His|Val|Leu|Ala|Phe|Ser|Lys|Ser|Cys|
| | | | |85| | | |90| | | | |95| | |
|His|Leu|Pro|Ala|Ala|Ser|Gly|Leu|Glu|Thr|Leu|Asp|Ser|Leu|Gly|Gly|
| | | |100| | | | |105| | | | |110| | |
|Val|Leu|Glu|Ala|Ser|Gly|Tyr|Ser|Thr|Glu|Val|Val|Ala|Leu|Ser|Arg|
| | |115| | | | |120| | | | |125| | | |
|Leu|Gln|Gly|Ser|Leu|Gln|Asp|Met|Leu|Trp|Gln|Leu|Asp|Leu|Ser|Pro|
| |130| | | | |135| | | |140| | | | | |
|Gly|Cys| | | | | | | | | | | | | | |
|145| | | | | | | | | | | | | | | |

( 2 ) INFORMATION FOR SEQ ID NO:7:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( v ) FRAGMENT TYPE: N-terminal ( x i ) SEQUENCE DESCRIPTION: SEQ ID NO:7:

| | | | | | | | | | | | | | | | |
|---|---|---|---|---|---|---|---|---|---|---|---|---|---|---|---|
|Val|Pro|Ile|Gln|Lys|Val|Gln|Asp|Asp|Thr|Lys|Thr|Leu|Ile|Lys|Thr|
|1| | | |5| | | | |10| | | | |15| |
|Ile|Val|Thr|Arg|Ile|Asn|Asp|Ile|Ser|His|Thr|Gln|Ser|Val|Ser|Ser|
| | | |20| | | | |25| | | | |30| | |
|Lys|Gln|Lys|Val|Thr|Gly|Leu|Asp|Phe|Ile|Pro|Gly|Leu|His|Pro|Ile|
| | |35| | | | |40| | | | |45| | | |
|Leu|Thr|Leu|Ser|Lys|Met|Asp|Gln|Thr|Leu|Ala|Val|Tyr|Gln|Gln|Ile|
| |50| | | | |55| | | | |60| | | | |
|Leu|Thr|Ser|Met|Pro|Ser|Arg|Asn|Val|Ile|Gln|Ile|Ser|Asn|Asp|Leu|
|65| | | |70| | | | |75| | | | | |80|
|Glu|Asn|Leu|Arg|Asp|Leu|Leu|His|Val|Leu|Ala|Phe|Ser|Lys|Ser|Cys|
| | | | |85| | | |90| | | | |95| | |
|His|Leu|Pro|Gln|Ala|Ser|Gly|Leu|Glu|Thr|Leu|Asp|Ser|Leu|Gly|Gly|
| | | |100| | | | |105| | | | |110| | |
|Val|Leu|Glu|Ala|Ser|Gly|Tyr|Ser|Thr|Glu|Val|Val|Ala|Leu|Ser|Arg|
| | |115| | | | |120| | | | |125| | | |
|Leu|Gln|Gly|Ser|Leu|Gln|Asp|Met|Leu|Trp|Gln|Leu|Asp|Leu|Ser|Pro|
| |130| | | | |135| | | |140| | | | | |
|Gly|Cys| | | | | | | | | | | | | | |
|145| | | | | | | | | | | | | | | |

( 2 ) INFORMATION FOR SEQ ID NO:8:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO (v) FRAGMENT TYPE: N-terminal (xi) SEQUENCE DESCRIPTION: SEQ ID NO:8:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |
| Ile | Val | Thr | Arg | Ile | Asn | Asp | Ile | Ser | His | Thr | Gln | Ser | Val | Ser | Ser |
| | | | 20 | | | | | 25 | | | | | 30 | | |
| Lys | Gln | Lys | Val | Thr | Gly | Leu | Asp | Phe | Ile | Pro | Gly | Leu | His | Pro | Ile |
| | | 35 | | | | | 40 | | | | | 45 | | | |
| Leu | Thr | Leu | Ser | Lys | Met | Asp | Gln | Thr | Leu | Ala | Val | Tyr | Gln | Gln | Ile |
| | 50 | | | | | 55 | | | | | 60 | | | | |
| Leu | Thr | Ser | Met | Pro | Ser | Arg | Asn | Val | Ile | Gln | Ile | Ser | Asn | Asp | Leu |
| 65 | | | | | 70 | | | | | 75 | | | | | 80 |
| Glu | Asn | Leu | Arg | Asp | Leu | Leu | His | Val | Leu | Ala | Phe | Ser | Lys | Ser | Cys |
| | | | | 85 | | | | | 90 | | | | | 95 | |
| His | Leu | Pro | Asp | Ala | Ser | Gly | Leu | Glu | Thr | Leu | Asp | Ser | Leu | Gly | Gly |
| | | | 100 | | | | | 105 | | | | | 110 | | |
| Val | Leu | Glu | Ala | Ser | Gly | Tyr | Ser | Thr | Glu | Val | Val | Ala | Leu | Ser | Arg |
| | | | 115 | | | | | 120 | | | | | 125 | | |
| Leu | Gln | Gly | Ser | Leu | Gln | Asp | Met | Leu | Trp | Gln | Leu | Asp | Leu | Ser | Pro |
| | | 130 | | | | | 135 | | | | | 140 | | | |
| Gly | Cys | | | | | | | | | | | | | | |
| 145 | | | | | | | | | | | | | | | |

(2) INFORMATION FOR SEQ ID NO:9:

(i) SEQUENCE CHARACTERISTICS:
       (A) LENGTH: 146 amino acids
       (B) TYPE: amino acid
       (C) STRANDEDNESS: single
       (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:9:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |
| Ile | Val | Thr | Arg | Ile | Asn | Asp | Ile | Ser | His | Thr | Gln | Ser | Val | Ser | Ser |
| | | | 20 | | | | | 25 | | | | | 30 | | |
| Lys | Gln | Lys | Val | Thr | Gly | Leu | Asp | Phe | Ile | Pro | Gly | Leu | His | Pro | Ile |
| | | 35 | | | | | 40 | | | | | 45 | | | |
| Leu | Thr | Leu | Ser | Lys | Met | Asp | Gln | Thr | Leu | Ala | Val | Tyr | Gln | Gln | Ile |
| | 50 | | | | | 55 | | | | | 60 | | | | |
| Leu | Thr | Ser | Met | Pro | Ser | Arg | Asn | Val | Ile | Gln | Ile | Ser | Asn | Asp | Leu |
| 65 | | | | | 70 | | | | | 75 | | | | | 80 |
| Glu | Asn | Leu | Arg | Asp | Leu | Leu | His | Val | Leu | Ala | Phe | Ser | Lys | Ser | Cys |
| | | | | 85 | | | | | 90 | | | | | 95 | |
| His | Leu | Pro | Glu | Ala | Ser | Gly | Leu | Glu | Thr | Leu | Asp | Ser | Leu | Gly | Gly |
| | | | 100 | | | | | 105 | | | | | 110 | | |
| Val | Leu | Glu | Ala | Ser | Gly | Tyr | Ser | Thr | Glu | Val | Val | Ala | Leu | Ser | Arg |
| | | | 115 | | | | | 120 | | | | | 125 | | |
| Leu | Gln | Gly | Ser | Leu | Gln | Asp | Met | Leu | Trp | Gln | Leu | Asp | Leu | Ser | Pro |
| | | 130 | | | | | 135 | | | | | 140 | | | |

```
                Gly   Cys
                145
```

( 2 ) INFORMATION FOR SEQ ID NO:10:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:10:

```
Val   Pro   Ile   Gln   Lys   Val   Gln   Asp   Asp   Thr   Lys   Thr   Leu   Ile   Lys   Thr
1                       5                             10                            15

Ile   Val   Thr   Arg   Ile   Asn   Asp   Ile   Ser   His   Thr   Gln   Ser   Val   Ser   Ser
                  20                            25                            30

Lys   Gln   Lys   Val   Thr   Gly   Leu   Asp   Phe   Ile   Pro   Gly   Leu   His   Pro   Asp
            35                            40                            45

Leu   Thr   Leu   Ser   Lys   Met   Asp   Gln   Thr   Leu   Ala   Val   Tyr   Gln   Gln   Ile
      50                            55                            60

Leu   Thr   Ser   Met   Pro   Ser   Arg   Asn   Val   Ile   Gln   Ile   Ser   Asn   Asp   Leu
65                            70                            75                            80

Glu   Asn   Leu   Arg   Asp   Leu   Leu   His   Val   Leu   Ala   Phe   Ser   Lys   Ser   Cys
                        85                            90                            95

His   Leu   Pro   Asp   Ala   Ser   Gly   Leu   Glu   Thr   Leu   Asp   Ser   Leu   Gly   Gly
                  100                           105                           110

Val   Leu   Glu   Ala   Ser   Gly   Tyr   Ser   Thr   Glu   Val   Val   Ala   Leu   Ser   Arg
            115                           120                           125

Leu   Gln   Gly   Ser   Leu   Gln   Asp   Met   Leu   Trp   Gln   Leu   Asp   Leu   Ser   Pro
      130                           135                           140

Gly   Cys
145
```

( 2 ) INFORMATION FOR SEQ ID NO:11:

( i ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:11:

```
Val   Pro   Ile   Gln   Lys   Val   Gln   Asp   Asp   Thr   Lys   Thr   Leu   Ile   Lys   Thr
1                       5                             10                            15

Ile   Val   Thr   Arg   Ile   Asp   Asp   Ile   Ser   His   Thr   Gln   Ser   Val   Ser   Ser
                  20                            25                            30

Lys   Gln   Lys   Val   Thr   Gly   Leu   Asp   Phe   Ile   Pro   Gly   Leu   His   Pro   Ile
            35                            40                            45
```

```
Leu  Thr  Leu  Ser  Lys  Met  Asp  Gln  Thr  Leu  Ala  Val  Tyr  Gln  Gln  Ile
     50                      55                      60

Leu  Thr  Ser  Met  Pro  Ser  Arg  Asn  Val  Ile  Gln  Ile  Ser  Asn  Asp  Leu
65                       70                      75                           80

Glu  Asn  Leu  Arg  Asp  Leu  Leu  His  Val  Leu  Ala  Phe  Ser  Lys  Ser  Cys
                    85                      90                      95

His  Leu  Pro  Trp  Ala  Ser  Gly  Leu  Glu  Thr  Leu  Asp  Ser  Leu  Gly  Gly
               100                      105                           110

Val  Leu  Glu  Ala  Ser  Gly  Tyr  Ser  Thr  Glu  Val  Val  Ala  Leu  Ser  Arg
          115                      120                      125

Leu  Gln  Gly  Ser  Leu  Gln  Asp  Met  Leu  Trp  Gln  Leu  Asp  Leu  Ser  Pro
          130                      135                      140

Gly  Cys
145
```

(2) INFORMATION FOR SEQ ID NO:12:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:12:

```
Val  Pro  Ile  Gln  Lys  Val  Gln  Asp  Asp  Thr  Lys  Thr  Leu  Ile  Lys  Thr
1               5                        10                          15

Ile  Val  Thr  Arg  Ile  Asn  Asp  Ile  Ser  His  Ala  Gln  Ser  Val  Ser  Ser
               20                   25                       30

Lys  Gln  Lys  Val  Thr  Gly  Leu  Asp  Phe  Ile  Pro  Gly  Leu  His  Pro  Ile
          35                        40                      45

Leu  Thr  Leu  Ser  Lys  Met  Asp  Gln  Thr  Leu  Ala  Val  Tyr  Gln  Gln  Ile
     50                      55                      60

Leu  Thr  Ser  Met  Pro  Ser  Arg  Asn  Val  Ile  Gln  Ile  Ser  Asn  Asp  Leu
65                       70                      75                           80

Glu  Asn  Leu  Arg  Asp  Leu  Leu  His  Val  Leu  Ala  Phe  Ser  Lys  Ser  Cys
                    85                      90                      95

His  Leu  Pro  Trp  Ala  Ser  Gly  Leu  Glu  Thr  Leu  Asp  Ser  Leu  Gly  Gly
               100                      105                           110

Val  Leu  Glu  Ala  Ser  Gly  Tyr  Ser  Thr  Glu  Val  Val  Ala  Leu  Ser  Arg
          115                      120                      125

Leu  Gln  Gly  Ser  Leu  Gln  Asp  Met  Leu  Trp  Gln  Leu  Asp  Leu  Ser  Pro
          130                      135                      140

Gly  Cys
145
```

(2) INFORMATION FOR SEQ ID NO:13:

(i) SEQUENCE CHARACTERISTICS:
        (A) LENGTH: 146 amino acids
        (B) TYPE: amino acid
        (C) STRANDEDNESS: single
        (D) TOPOLOGY: linear (ii) MOLECULE TYPE: protein (  i i i  ) HYPOTHETICAL: NO (  i v  ) ANTI-SENSE: NO (  v  ) FRAGMENT TYPE: N-terminal (  x i  ) SEQUENCE DESCRIPTION: SEQ ID NO:13:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |
| Ile | Val | Thr | Arg | Ile | Asn | Asp | Ile | Ser | His | Thr | Gln | Ser | Val | Ser | Ser |
| | | | 20 | | | | | 25 | | | | | 30 | | |
| Lys | Gln | Lys | Val | Thr | Gly | Leu | Asp | Phe | Ile | Pro | Gly | Leu | His | Pro | Ile |
| | | 35 | | | | | 40 | | | | | 45 | | | |
| Leu | Thr | Leu | Ser | Lys | Met | Asp | Gln | Thr | Leu | Ala | Val | Tyr | Gln | Gln | Ile |
| | 50 | | | | | 55 | | | | | 60 | | | | |
| Leu | Thr | Ser | Met | Pro | Ser | Arg | Asn | Val | Ile | Gln | Ile | Ser | Asn | Asp | Leu |
| 65 | | | | | 70 | | | | | 75 | | | | | 80 |
| Glu | Asn | Leu | Arg | Asp | Leu | Leu | His | Val | Leu | Ala | Phe | Ser | Lys | Ser | Cys |
| | | | | 85 | | | | | 90 | | | | | 95 | |
| His | Leu | Pro | Trp | Ala | Ser | Gly | Leu | Glu | Thr | Leu | Asp | Ser | Leu | Gly | Gly |
| | | | 100 | | | | | 105 | | | | | 110 | | |
| Val | Leu | Glu | Ala | Ser | Gly | Tyr | Ser | Thr | Glu | Val | Val | Ala | Leu | Ser | Arg |
| | | 115 | | | | | 120 | | | | | 125 | | | |
| Leu | Gln | Gly | Ser | Leu | Gln | Asp | Met | Leu | Gln | Gln | Leu | Asp | Leu | Ser | Pro |
| | 130 | | | | | 135 | | | | | 140 | | | | |
| Gly | Cys |
| 145 | |

( 2 ) INFORMATION FOR SEQ ID NO:14:

(  i  ) SEQUENCE CHARACTERISTICS:
        ( A ) LENGTH: 146 amino acids
        ( B ) TYPE: amino acid
        ( C ) STRANDEDNESS: single
        ( D ) TOPOLOGY: linear (  i i  ) MOLECULE TYPE: protein (  i i i  ) HYPOTHETICAL: NO (  i v  ) ANTI-SENSE: NO (  v  ) FRAGMENT TYPE: N-terminal (  x i  ) SEQUENCE DESCRIPTION: SEQ ID NO:14:

| Val | Pro | Ile | Gln | Lys | Val | Gln | Asp | Asp | Thr | Lys | Thr | Leu | Ile | Lys | Thr |
|---|---|---|---|---|---|---|---|---|---|---|---|---|---|---|---|
| 1 | | | | 5 | | | | | 10 | | | | | 15 | |
| Ile | Val | Thr | Arg | Ile | Asn | Asp | Ile | Ser | His | Thr | Gln | Ser | Val | Ser | Ser |
| | | | 20 | | | | | 25 | | | | | 30 | | |
| Lys | Gln | Lys | Val | Thr | Gly | Leu | Asp | Phe | Ile | Pro | Gly | Leu | His | Pro | Ile |
| | | 35 | | | | | 40 | | | | | 45 | | | |
| Leu | Thr | Leu | Ser | Lys | Met | Asp | Gln | Thr | Leu | Ala | Val | Tyr | Gln | Gln | Ile |
| | 50 | | | | | 55 | | | | | 60 | | | | |
| Leu | Thr | Ser | Met | Pro | Ser | Arg | Asn | Val | Ile | Gln | Ile | Ser | Asn | Asp | Leu |
| 65 | | | | | 70 | | | | | 75 | | | | | 80 |
| Glu | Asn | Leu | Arg | Asp | Leu | Leu | His | Val | Leu | Ala | Phe | Ser | Lys | Ser | Cys |
| | | | | 85 | | | | | 90 | | | | | 95 | |
| His | Leu | Pro | Gln | Ala | Ser | Gly | Leu | Glu | Thr | Leu | Asp | Ser | Leu | Gly | Gly |
| | | | 100 | | | | | 105 | | | | | 110 | | |
| Val | Leu | Glu | Ala | Ser | Gly | Tyr | Ser | Thr | Glu | Val | Val | Ala | Leu | Ser | Arg |

|           |           | 115       |           |           |           | 120       |           |           |           | 125       |           |           |           |
|-----------|-----------|-----------|-----------|-----------|-----------|-----------|-----------|-----------|-----------|-----------|-----------|-----------|-----------|
| Leu | Gln | Gly | Ser | Leu | Gln | Asp | Met | Leu | Gln | Gln | Leu | Asp | Leu | Ser | Pro |
|     | 130 |     |     |     |     | 135 |     |     |     |     | 140 |     |     |     |     |

Gly Cys
145

(2) INFORMATION FOR SEQ ID NO:15:

(i) SEQUENCE CHARACTERISTICS:
      (A) LENGTH: 146 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:15:

Val Pro Ile Gln Lys Val Gln Asp Asp Thr Lys Thr Leu Ile Lys Thr
1               5                       10                      15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                      75                  80

Glu Asn Leu Arg Asp Leu Leu His Val Leu Ala Phe Ser Lys Ser Cys
                85                  90                  95

His Leu Pro Ala Ala Ser Gly Leu Glu Thr Leu Asp Ser Leu Gly Gly
                100                 105                 110

Val Leu Glu Ala Ser Gly Tyr Ser Thr Glu Val Val Ala Leu Ser Arg
            115                 120                 125

Leu Gln Gly Ser Leu Gln Asp Met Leu Gln Gln Leu Asp Leu Ser Pro
    130                 135                 140

Gly Cys
145

(2) INFORMATION FOR SEQ ID NO:16:

(i) SEQUENCE CHARACTERISTICS:
      (A) LENGTH: 146 amino acids
      (B) TYPE: amino acid
      (C) STRANDEDNESS: single
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:16:

Val Pro Ile Gln Lys Val Gln Asp Asp Thr Lys Thr Leu Ile Lys Thr
1               5                       10                      15

Ile Val Thr Arg Ile Asn Asp Ile Ser His Thr Gln Ser Val Ser Ser

|     |     |     | 20  |     |     |     | 25  |     |     |     | 30  |     |     |     |
| --- | --- | --- | --- | --- | --- | --- | --- | --- | --- | --- | --- | --- | --- | --- |
| Lys | Gln | Lys<br>35 | Val | Thr | Gly | Leu | Asp<br>40 | Phe | Ile | Pro | Gly | Leu<br>45 | His | Pro | Ile |
| Leu | Thr<br>50 | Leu | Ser | Lys | Met | Asp<br>55 | Gln | Thr | Leu | Ala | Val<br>60 | Tyr | Gln | Gln | Ile |
| Leu<br>65 | Thr | Ser | Met | Pro | Ser<br>70 | Arg | Asp | Val | Ile | Gln<br>75 | Ile | Ser | Asn | Asp | Leu<br>80 |
| Glu | Asn | Leu | Arg | Asp<br>85 | Leu | Leu | His | Val | Ala<br>90 | Leu | Ala | Phe | Ser | Lys<br>95 | Ser | Cys |
| His | Leu | Pro | Asp<br>100 | Ala | Ser | Gly | Leu | Glu<br>105 | Thr | Leu | Asp | Ser | Leu<br>110 | Gly | Gly |
| Val | Leu | Glu<br>115 | Ala | Ser | Gly | Tyr | Ser<br>120 | Thr | Glu | Val | Val | Ala<br>125 | Leu | Ser | Arg |
| Leu | Gln<br>130 | Gly | Ser | Leu | Gln | Asp<br>135 | Met | Leu | Trp | Gln | Leu<br>140 | Asp | Leu | Ser | Pro |
| Gly<br>145 | Cys |     |     |     |     |     |     |     |     |     |     |     |     |     |     |

( 2 ) INFORMATION FOR SEQ ID NO:17:

( i ) SEQUENCE CHARACTERISTICS:
        ( A ) LENGTH: 148 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:17:

| Met<br>1 | Arg | Val | Pro | Ile<br>5 | Gln | Lys | Val | Gln | Asp<br>10 | Asp | Thr | Lys | Thr | Leu<br>15 | Ile |
| --- | --- | --- | --- | --- | --- | --- | --- | --- | --- | --- | --- | --- | --- | --- | --- |
| Lys | Thr | Ile | Val<br>20 | Thr | Arg | Ile | Asn | Asp<br>25 | Ile | Ser | His | Thr | Gln<br>30 | Ser | Val |
| Ser | Ser | Lys<br>35 | Gln | Lys | Val | Thr | Gly<br>40 | Leu | Asp | Phe | Ile | Pro<br>45 | Gly | Leu | His |
| Pro | Ile<br>50 | Leu | Thr | Leu | Ser | Lys<br>55 | Met | Asp | Gln | Thr | Leu<br>60 | Ala | Val | Tyr | Gln |
| Gln<br>65 | Ile | Leu | Thr | Ser | Met<br>70 | Pro | Ser | Arg | Asn | Val<br>75 | Ile | Gln | Ile | Ser | Asn<br>80 |
| Asp | Leu | Glu | Asn | Leu<br>85 | Arg | Asp | Leu | Leu | His<br>90 | Val | Leu | Ala | Phe | Ser<br>95 | Lys |
| Ser | Cys | His | Leu<br>100 | Pro | Ala | Ala | Ser | Gly<br>105 | Leu | Glu | Thr | Leu | Asp<br>110 | Ser | Leu |
| Gly | Gly | Val<br>115 | Leu | Glu | Ala | Ser | Gly<br>120 | Tyr | Ser | Thr | Glu | Val<br>125 | Val | Ala | Leu |
| Ser | Arg<br>130 | Leu | Gln | Gly | Ser | Leu<br>135 | Gln | Asp | Met | Leu | Trp<br>140 | Gln | Leu | Asp | Leu |
| Ser<br>145 | Pro | Gly | Cys |     |     |     |     |     |     |     |     |     |     |     |     |

( 2 ) INFORMATION FOR SEQ ID NO:18:

( i ) SEQUENCE CHARACTERISTICS:
        ( A ) LENGTH: 148 amino acids (B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:18:

| Met | Arg | Val | Pro | Ile | Gln | Lys | Val | Gln | Asp | Asp | Thr | Lys | Thr | Leu | Ile |
|---|---|---|---|---|---|---|---|---|---|---|---|---|---|---|---|
| 1 | | | | 5 | | | | | 10 | | | | | 15 | |
| Lys | Thr | Ile | Val | Thr | Arg | Ile | Asn | Asp | Ile | Ser | His | Thr | Gln | Ser | Val |
| | | | 20 | | | | | 25 | | | | | 30 | | |
| Ser | Ser | Lys | Gln | Lys | Val | Thr | Gly | Leu | Asp | Phe | Ile | Pro | Gly | Leu | His |
| | | 35 | | | | | 40 | | | | | 45 | | | |
| Pro | Ile | Leu | Thr | Leu | Ser | Lys | Met | Asp | Gln | Thr | Leu | Ala | Val | Tyr | Gln |
| | 50 | | | | | 55 | | | | | 60 | | | | |
| Gln | Ile | Leu | Thr | Ser | Met | Pro | Ser | Arg | Asn | Val | Ile | Gln | Ile | Ser | Asn |
| 65 | | | | | 70 | | | | | 75 | | | | | 80 |
| Asp | Leu | Glu | Asn | Leu | Arg | Asp | Leu | Leu | His | Val | Leu | Ala | Phe | Ser | Lys |
| | | | | 85 | | | | | 90 | | | | | 95 | |
| Ser | Cys | His | Leu | Pro | Trp | Ala | Ser | Gly | Leu | Glu | Thr | Leu | Asp | Ser | Leu |
| | | | 100 | | | | | 105 | | | | | 110 | | |
| Gly | Gly | Val | Leu | Glu | Ala | Ser | Gly | Tyr | Ser | Thr | Glu | Val | Val | Ala | Leu |
| | | 115 | | | | | 120 | | | | | 125 | | | |
| Ser | Arg | Leu | Gln | Gly | Ser | Leu | Gln | Asp | Met | Leu | Trp | Gln | Leu | Asp | Leu |
| | 130 | | | | | 135 | | | | | 140 | | | | |
| Ser | Pro | Gly | Cys | | | | | | | | | | | | |
| 145 | | | | | | | | | | | | | | | |